(12) United States Patent
Jones

(10) Patent No.: US 7,248,370 B2
(45) Date of Patent: Jul. 24, 2007

(54) METHOD TO REDUCE BACKGROUND NOISE IN A SPECTRUM

(75) Inventor: Christopher M. Jones, Missouri City, TX (US)

(73) Assignee: Caleb Brett USA, Inc., Houston, TX (US)

(*) Notice: Subject to any disclaimer, the term of this patent is extended or adjusted under 35 U.S.C. 154(b) by 27 days.

(21) Appl. No.: 11/222,240

(22) Filed: Sep. 8, 2005

(65) Prior Publication Data

US 2006/0197957 A1 Sep. 7, 2006

Related U.S. Application Data

(63) Continuation-in-part of application No. 11/074,319, filed on Mar. 7, 2005.

(51) Int. Cl.
G01B 9/02 (2006.01)
G01J 3/45 (2006.01)

(52) U.S. Cl. .................................................... 356/454

(58) Field of Classification Search ................ 356/300, 356/450, 451, 454, 519; 250/550
See application file for complete search history.

(56) References Cited

U.S. PATENT DOCUMENTS

| 5,317,156 A | * | 5/1994 | Cooper et al. | ............. | 250/345 |
|---|---|---|---|---|---|
| 5,841,533 A | * | 11/1998 | Atkinson | ..................... | 356/326 |
| 6,040,578 A | | 3/2000 | Malin et al. | | |
| 6,483,589 B1 | * | 11/2002 | Suzuki et al. | ............... | 356/437 |
| 6,639,678 B1 | | 10/2003 | Veale | | |
| 2003/0200040 A1 | | 10/2003 | Trygg et al. | | |
| 2004/0064259 A1 | | 4/2004 | Haaland et al. | | |
| 2004/0164237 A1 | * | 8/2004 | Jones et al. | ............... | 250/269.1 |
| 2006/0197956 A1 | * | 9/2006 | Jones | ......................... | 356/454 |

FOREIGN PATENT DOCUMENTS

WO        WO 92/07275        4/1992

OTHER PUBLICATIONS

International Search Report and Written Opinion, Jun. 29, 2006.

* cited by examiner

*Primary Examiner*—Gregory J. Toatley
*Assistant Examiner*—Michael A. Lyons
(74) *Attorney, Agent, or Firm*—Carella, Byrne, Bain, etal; Elliot M. Olstein; William Squire

(57) ABSTRACT

An embodiment includes a method to reduce background noise in a spectrum. A further embodiment includes a method to reduce, by at least about two orders of magnitude, background noise in an experimental absorbance spectrum. Further, an embodiment includes a machine-readable medium that provides instructions, which when executed by a machine, reduce background noise in a spectrum. Further, an embodiment includes a machine-readable medium that provides instructions, which when executed by a machine, reduce, by at least two orders of magnitude, background noise in an experimental absorbance spectrum.

44 Claims, 23 Drawing Sheets

METHOD TO REDUCE BACKGROUND NOISE IN A SPECTRUM

RELATED APPLICATION

This application is a continuation-in-part (CIP) application of U.S. application Ser. No. 11/074,319, filed on Mar. 7, 2005.

FIELD OF TECHNOLOGY

Embodiments of the present invention relate to the field of spectroscopy. Specifically, embodiments relate to the reduction of background noise in a spectrum.

BACKGROUND OF THE INVENTION

The value of spectroscopy as an analytical tool is limited by its accuracy and reliability. Although spectroscopy can be used to identify and quantify substances in many environments and applications, different types of interferences can detrimentally influence the extraction of useful information from a spectrum. One type of interference, characterized as etalon noise, behaves chaotically and can disguise or distort accurate data. Etalons are patterns of light caused by reflections in the optical path of the source used in the spectroscopic technique. The etalons can cause constructive and destructive interference with the signal at certain wavelengths of light.

Traditionally, efforts to reduce etalon noise have focused either on the physical design of the spectroscopic device or on mathematical modeling. Both areas have seen repeated failures. Etalons could, theoretically, be minimized by creating the optimal instrument design, but progress in this area has stalled for a number of years. In addition, attempts have been made to derive a mathematical formula describing the behavior of the etalons. Unfortunately, the etalons can instantaneously change configurations to give multiple allowable solutions to a formula.

Regardless of which traditional approach is used to characterize etalon noise, they are inaccurate and slow. In a specific application, such as oil drilling, spectroscopy is used to detect subterranean gases in real-time. The previous methods do not allow for computation at speeds needed for real time measurements. Calibration of the instrument takes too long and as the instrument may be located hundreds of feet below the surface of the earth in a hole, it would be inaccessible for calibration and adjustment. A solution is needed that reduces the etalon noise in a spectrum in a quick, reliable way.

SUMMARY OF THE INVENTION

Embodiments of the present invention provide a method to reduce background noise in an experimental spectrum. By uniquely combining techniques used in physical spectroscopy and chemometrics, noise can be reduced in a way and magnitude not previously experienced. The embodiments allow for more reliable spectroscopic measurements, especially of trace substances not previously detected accurately due to noise interfering with their spectral features. In addition to the advances made in detecting trace substances, the use of the embodiments can increase the accurate detection of all target species in a spectrum by creating a simulation spectrum that more closely matches the experimental spectrum. The simulation spectrum allows for more accurate determinations of the presence and concentrations of target species. Such results not only allow for more accurate determinations of the concentrations of target species from spectra, but for more reliable readings taken at speeds up to real-time. The present embodiments provide a method to correct for background noise in real-time, as opposed to previous methods that attempted to adjust for the background noise on an order of minutes. Further, embodiments of the invention simplify or reduce the steps used to characterize an etalon background in a spectrum. The embodiments of the present invention increase the value and use of spectroscopy for all types of public and private applications.

The embodiments of the present invention directly increase the flexibility, reliability and accuracy of spectroscopy. The embodiments apply to any use of spectroscopy. Spectroscopy is typically used in hundreds of different applications. In the environmental field, spectroscopic measurements could be enhanced when detecting drinking water pollutants, measuring smog or air quality, and analyzing toxins in soil. Military applications vary from identifying vehicles by the spectroscopic signature in the vehicle's paint to the search for weapons of mass destruction by analyzing suspected storage area materials. The embodiments can be utilized in industrial process plants. Batch quality can be more quickly and accurately monitored in-line without delay or interruption in the process. Medically, spectroscopy can be used for detecting such trace substances as glucose in blood for more reliable sensors used by diabetics. Within the oil industry, spectroscopy can be used downhole to analyze formation composition. Whether in academia or in industry, the use of spectroscopy as an analytical technique can be greatly amplified by the application of the embodiments of the present invention.

The present invention provides a method to reduce background noise in an experimental spectrum. The method includes the steps of: contacting a blank sample with electromagnetic radiation, sufficient to obtain a background spectrum; performing an intrinsic dimension analysis on the background spectrum, sufficient to obtain multiple correlations between variables in the background spectrum; identifying and retaining the intrinsic dimensionality of the variables in the background spectrum; contacting an experimental sample with electromagnetic radiation, sufficient to obtain an experimental spectrum; performing a regression analysis on the experimental spectrum, based upon known characteristics of pure substances, effective to provide a simulation spectrum; mathematically operating at least part of the simulation spectrum with at least part of the experimental spectrum, effective to provide a residual spectrum; projecting at least part of the residual spectrum onto the intrinsic dimensionality of the background spectrum, effective to identify any etalons present in the residual spectrum; mathematically operating the etalon with the experimental spectrum, effective to provide an experimental spectrum having reduced background noise.

The present invention also provides a method to reduce, by at least about 2 orders of magnitude, background noise in an experimental absorbance spectrum. The method includes the steps of: contacting a blank sample with infrared energy, sufficient to obtain a background spectrum; performing a principal component analysis (PCA) on the background spectrum, sufficient to obtain multiple correlations between variables in the background spectrum; identifying and retaining the intrinsic dimensionality of the variables in the background spectrum; contacting an experimental sample with infrared energy, sufficient to obtain an experimental spectrum; performing a multivariate curve resolution-alternating least squares (MCR-ALS) analysis on the experimental spectrum, based upon known characteristics of pure substances, effective to provide a simulation spectrum; subtracting at least part of the simulation spectrum from at least part of the experimental spectrum, effective to provide a residual spectrum; projecting at least part of the residual spectrum onto the intrinsic dimensionality of the background spectrum, effective to identify any etalons present in the residual spectrum; removing the etalon from the experimental spectrum, effective to provide an experimental spectrum having reduced background noise.

The present invention also provides a machine-readable medium that provides instructions, which when executed by a machine, cause said machine to perform operations including the steps of: contacting a blank sample with electromagnetic radiation, sufficient to obtain a background spectrum; performing an intrinsic dimension analysis on a background spectrum, sufficient to obtain multiple correlations between variables in the background spectrum; identifying and retaining the intrinsic dimensionality of the variables in the background spectrum; contacting an experimental sample with electromagnetic radiation, sufficient to obtain an experimental spectrum; performing a regression analysis on the experimental spectrum, based upon known characteristics of pure substances, effective to provide a simulation spectrum; mathematically operating at least part of the simulation spectrum with at least part of the experimental spectrum, effective to provide a residual spectrum; projecting at least part of the residual spectrum onto the intrinsic dimensionality of the background spectrum, effective to identify any etalons present in the residual spectrum; mathematically operating the etalon with the experimental spectrum, effective to provide an experimental spectrum having reduced background noise.

The present invention also provides a machine-readable medium that provides instructions, which when executed by a machine, cause said machine to perform operations comprising: contacting a blank sample with infrared energy, sufficient to obtain a background spectrum; performing a principal component analysis (PCA) on the background spectrum, sufficient to obtain multiple correlations between variables in the background spectrum; identifying and retaining the intrinsic dimensionality of the variables in the background spectrum; contacting an experimental sample with infrared energy, sufficient to obtain an experimental spectrum; performing a multivariate curve resolution-alternating least squares (MCR-ALS) analysis on the experimental spectrum, based upon known characteristics of pure substances, effective to provide a simulation spectrum; subtracting at least part of the simulation spectrum from at least part of the experimental spectrum, effective to provide a residual spectrum; projecting at least part of the residual spectrum onto the intrinsic dimensionality of the background spectrum, effective to identify any etalons present in the residual spectrum; removing the etalon from the experimental spectrum, effective to provide an experimental spectrum having reduced background noise.

BRIEF DESCRIPTION OF THE DRAWINGS

Embodiments of the invention may be best understood by referring to the following description and accompanying drawings which illustrate such embodiments. The numbering scheme for the Figures included herein are such that the leading number for a given reference number in a Figure is associated with the number of the Figure. Reference numbers are the same for those elements that are the same across different Figures. For example, a block flow diagram depicting the blank sample (1) can be located in FIG. 1. However, reference numbers are the same for those elements that are the same across different Figures. In the drawings.

DETAILED DESCRIPTION OF THE EMBODIMENTS OF THE PRESENT INVENTION

Figure 1:
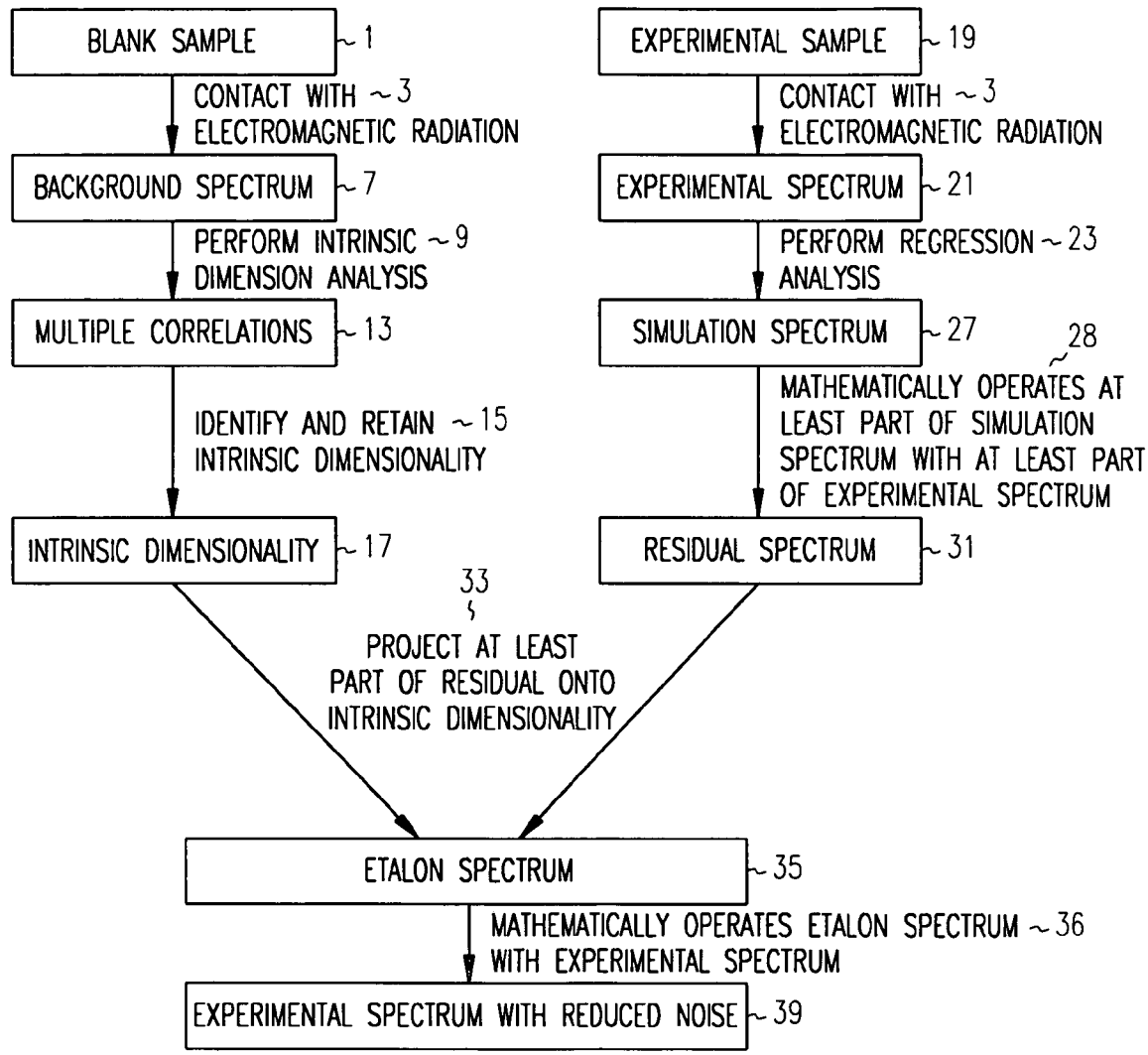
FIG. 1 illustrates a block flow diagram depicting the reduction of noise in a spectrum collected by spectroscopy.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The embodiments of the present invention relate to novel methods to reduce background noise in an experimental spectrum. When describing the methods, the following terms have the following meanings, unless otherwise indicated.

Definitions

As used herein, "blank sample" refers to a sample tested, in the absence of the target species, under experimental conditions. In spectroscopy, the blank sample will typically be an empty cell or line, emptied by vacuum; or may contain only the ambient background substance, such as air or water. Further, in certain embodiments, the blank sample could contain Helium, Nitrogen or Argon.

As used herein, "electromagnetic radiation" refers to a form of energy transmission through a vacuum or a medium in which electric and magnetic fields are propagated as waves. Further, it includes visible light, infrared, ultraviolet, X-ray and radio waves. Petrucci, Ralph H. and Harwood, William S., *General Chemistry*, 6$^{th}$ Ed., New York 1993, p. 280.

As used herein, "wavelength" refers to the distance between the tops of two successive crests of a wave. In spectroscopy, substances react with energy at different wavelengths in different ways. The absorbance, emission, reflection or other properties of a substance depend on the wavelength of energy in which it is interacting. Petrucci, Ralph H. and Harwood, William S., *General Chemistry*, 6$^{th}$ Ed., New York 1993, p. 280.

As used herein, "noise" refers to extraneous, fluctuating signals which can include structured and/or random components which can interfere with desired signals. Noise can be present in the absence or presence of sample and/or analyte, and can be affected by sample or analyte.

As used herein, "spectroscopy" refers to the science that deals with the interactions of various types of radiation with matter. A radiation source first interacts with a sample. A detector then records the type of interaction, such as absorbance, transmittance or emission. The electrical signals from the detector are converted to useful numbers or a visual display such as a spectrum. Skoog, Douglas A., et. al., *Principles of Instrumental Analysis*, 5$^{th}$ Ed., Philadelphia 1998, p. 116. Examples of types of spectroscopy devices used may include Fourier Transform Infrared Spectrometers (FTIR) and Tunable Diode Laser Spectrometers (TDLS).

As used herein "spectrum" refers to an ordered array of the components of an emission or wave. The detection of a radiation after interacting with a sample is usually displayed graphically as a function of absorbance, emission, etc. versus wavelength or wavenumber.

As used herein, "absorbance spectrum" refers to a plot of some function of the attenuation of a beam of radiation versus wavelength, frequency, or wavenumber. Two methods of quantitatively measuring beam attenuation are transmittance and absorbance. Skoog, Douglas A., et. al., *Fundamentals of Analytical Chemistry*, 7$^{th}$ Ed., New York 1996, p. 503.

As used herein, "infrared energy" refers to radiation in the electromagnetic spectrum with wavenumbers ranging from about 12,800 to about 10 cm$^{-1}$ or wavelengths from about 0.78 to about 1000 μm. Further, mid-infrared energy refers to the range of about 2.5 about 50 μm or about 4000 to about 200 cm$^{-1}$. Further, near-infrared energy refers to the range of about 0.78 to about 2.5 μm or about 12,800 to about 4000 cm$^{-1}$. Skoog, Douglas A., et. al., *Fundamentals of Analytical Chemistry*, 7$^{th}$ Ed., New York 1996, p. 380-381.

As used herein, "regression" refers to the relationship between selected values of x and observed values of y (from which the most probable value of y can be predicted for any value of x). Therefore, "regression analysis" refers to the use of regression to make quantitative predictions of one variable from the values of another. Regression methods are frequently used to develop equations or simulation models from data sets in order to extract relevant information.

As used herein, "background" refers to the detector response or measurement in absence of sample, or in presence of sample but absence of analyte. Background may include a baseline and/or noise.

As used herein, "background noise" refers to the noise component of background.

As used herein, "analyte" or "target species" refers to the one or more phenomena to be observed or measured using spectroscopy and may include, without limitation, chemical species.

As used herein, "pure substances" refer to known spectral species. Pure substances may include the target species and any contaminants in a mixture. For example, in the oil industry, the pure substances may be a target species, such as methane, but also contaminants, such as ethane, propane and pentane. Any substance that has known spectral characteristics and may be anticipated in a sample may be a pure substance.

As used herein, "intermolecular" refers to existing or acting between molecules. Intermolecular forces are a result of differently charged atoms or molecules coming into contact or near contact.

As used herein, "concentration" refers to the amount of solute (substance dissolved) divided by the total amount of solvent (substance that dissolves) or the quantity of a substance per unit volume or weight. Concentration can be measured as moles per liter (amount divided by volume). Petrucci, Ralph H. and Harwood, William S., *General Chemistry*, 6$^{th}$ Ed., New York 1993, p. A34.

As used herein, "correlations" refer to statistics representing how closely variables co-vary. A correlation analysis measures the closeness of relationship between variables. Bennett, H., *Concise Chemical and Technical Dictionary*, $4^{th}$ Edition, New York, 1986 p. 342. In statistics, variables that directly correlate with each other have a value of one. In contrast, variables that have no correlation have a value of zero. Therefore, the correlations of variables will typically have a value between 0 and about 1, inclusive.

As used herein, "vector" refers to a variable quantity that can be resolved into components. Vectors typically have a quantitative value and a direction.

As used herein "source" refers to a process by which energy or a substance enters a system. In spectroscopy, a source usually refers to the radiation source such as a laser. The source may produce broadband or one or more distinct wavelengths. Further, the source may output energy in single or multiple shots or impulses of energy or may scan through a series or continuum of wavelengths.

As used herein "laser" refers to an acronym for Light Amplification by Stimulated Emission of Radiation; an optical device that produces an intense monochromatic beam of coherent light. Lasers are frequently used as radiation sources in spectroscopy.

As used herein "static" refers to the sample not moving. When using a static cell or housing in spectroscopy, the cell is temporary or permanently mounted and the sample does not move throughout the testing. Further, the embodiment could include a partially closed container, e.g. a cup without a top.

As used herein "in-line" refers to the sample moving. Samples that are in-line, may move through a tube or pipe and may be sampled as they move.

As used herein "residual" refers to the quantity left over at the end of a process. Morris, William, *The American Heritage Dictionary of the English Language*, Boston, 1981 p. 1106. Residual spectra are produced from the subtraction of one spectrum from another. The residual can be a set of numbers that can be graphed to produce a residual spectrum.

As used herein "signal-to-noise ratio" refers to the ratio of signal intensity to noise intensity. The signal is produced from the source and refers to the intensity as it is collected by the detector (post sample).

As used herein "intensity" refers to the energy transferred by a wave per unit time across a unit area perpendicular to the direction of propagation. Morris, William, *The American Heritage Dictionary of the English Language*, Boston, 1981 p. 682.

As used herein "variable" refers to a quantity that is subject to variation. Morris, William, *The American Heritage Dictionary of the English Language*, Boston, 1981 p. 1417. Variables in spectroscopy are numerous, but include concentration of sample, absorbance, emission, wavelength, frequency, wavenumber, etc.

As used herein "intrinsic dimensionality analysis" refers to the identification of the number of degrees of freedom inherent to a data set. The intrinsic dimensionality analysis includes methods that identify the vectors and correlations within variables in the data. The intrinsic dimensionality of a system refers to its inherent relationships between variables.

As used herein "principal component analysis" refers to attempts to determine a smaller set of synthetic variables that could explain the original set. Principal component analysis breaks data sets into components that describe and rank the correlations present. The strongest components are then used to more simply describe the data.

As used herein "degrees of freedom" refers to each independent mode in which a particle or system may move or be oriented.

As used herein "wavelet analysis" refers to an analysis of transforms that consider a function (taken to be a function of time) in terms of oscillations which are localized in both time and frequency.

As used herein "pattern recognition technique" refers to the process of identifying structure in data by comparison to known structure. Patterns are typically described in terms of multidimensional data vectors, where each component is called a feature. The aim of a pattern recognition system is to associate each pattern with one of the possible pattern classes.

As used herein "neural network" refers to a massively parallel collection of small and simple processing units where the interconnections form a large part of the network's intelligence.

As used herein "multivariate curve resolution-alternating least squares" refers to a flexible two-way data analysis method based on the assumption of Lambert-Beer's Law (concentration of a species is proportional to its absorbance) to perform a regression. Experimental matrices and pure component matrices are compared as to the species' contributions and the data optimized iteratively using the alternating least squares statistical method to produce a simulation data set that closely reflects the unknown experimental set.

As used herein "singular value decomposition" refers to a widely used technique to decompose a matrix into several component matrices, exposing many of the useful and interesting properties of the original matrix. SVD can determine the rank of matrix, quantify the sensitivity of a linear system to numerical error, or obtain an optimal lower-rank approximation to the matrix. SVD can split a vector space into lower-dimensional subspaces. SVD is a factorization of the rectangular real or complex matrix analogous diagonalization of symmetry or Hermitian square matrices using a basis of eigenvectors.

As used herein "etalon" refers to a varying transmission function caused by interference between the multiple reflections of light between reflecting surfaces. Etalons combine with the desired signal to cause unwanted constructive and destructive interference.

As used herein "simulation spectrum" refers to a spectrum that attempts to model an experimental spectrum by using known spectra of pure substances. The pure substances may be used as a baseline and may be made up of multiple known components, such as an uncontaminated hydrocarbon mixture from a refinery which does not vary over the relevant duration and is locally homogeneous. The simulation spectrum is calculated using a regression technique.

As used herein "experimental spectrum" refers to a spectrum produced from an experimental sample. The experimental sample contains the target species, but may contain many other species.

As used herein "etalon spectrum" refers to a spectrum produced from the projection of at least part of a residual spectrum onto the intrinsic dimensionality of a background spectrum.

As used herein "project" refers to casting a mathematical shadow of a data set onto another data set in order to define new dimensions and determine the root dimensionality of the system.

As used herein "subtracting" refers to conducting a mathematical operation on some number of data sets in which the result is a residual of the data sets.

As used herein "mathematically operating" refers to calculating by mathematical methods.

As used herein "interferent" refers to a substance that can interfere with the measurement of the target species. Interferents may have features that are similar to a target species when interacting with the source and therefore disguise the desired information.

As used herein "eigenfactor analysis" refers to a method to characterize the correlational structure among large sets of objects or data. By identifying the more dominant correlations in a data set, the set can be reduced to information that describes the strongest relationships between variables.

As used herein "linear regression" refers to attempts to model the relationship between two variables by fitting a linear equation to observed data. One variable is considered to be an explanatory variable, and the other is considered to be a dependent variable. The fitted (predicted) value of the response variable Y is a linear combination of the values of one or more predictor (X) variables.

As used herein "non-linear regression" refers to a regression in which the fitted (predicted) value of the response variable is a nonlinear function of one or more X variables. The non-linear regression model predicts values of Y from values of X using an equation that is not linear, nor can be adapted to a linear function by transforming Y.

As used herein "linear least squares" refers to a technique that attempts to find a "best fit" to a set of data by attempting to minimize the sum of the squares of the errors between the fitted function (Y values) and the data (X values) using a linear function.

As used herein "solution of simultaneous equations" refers to the solving of a set of equations in two or more variables for which there are values that can satisfy all the equations simultaneously.

As used herein "non-linear least squares" refers to a technique that attempts to find a "best fit" to a set of data by attempting to minimize the sum of the squares of the errors between the fitted function (Y values) and the data (X values) using a non-linear function.

As used herein "partial least squares" refers to a method which attempts to establish a relationship between the two matrices X and Y. The procedure is as follows: first, the principal components for X and Y are calculated separately (cf. PCA). The scores of the matrix X are then used for a regression model to predict the scores of Y which can then be used to predict Y. Partial least squares can be used interchangeably with "projection of latent structures."

Referring to FIGS. 1-4, novel methods to reduce background noise in an experimental spectrum are provided. The embodiments of the present invention include a method to reduce background noise in an experimental spectrum (FIG. 1). A blank sample (1) can be contacted with electromagnetic radiation (3) sufficient to obtain a background spectrum (7). An intrinsic dimension analysis can be performed (9) on the background spectrum (7) sufficient to obtain multiple correlations (13) between variables in the background spectrum (7). The intrinsic dimensionality (17) of the background spectrum (7) can be identified and retained (15). An experimental sample (19) can be contacted with electromagnetic radiation (3) sufficient to obtain an experimental spectrum (21). A regression analysis can be performed (23) on the experimental spectrum (21), based upon known characteristics of pure substances (19), effective to provide a simulation spectrum (27). At least part of the simulation spectrum (27) can be mathematically operated (28) with at least part of the experimental spectrum (21), effective to provide a residual spectrum (31). At least part of the residual spectrum (31) can be projected (33) onto the intrinsic dimensionality (17) of the background spectrum (7), effective to identify any etalons present in the residual spectrum (35). The etalon (35) can be mathematically operated (36) with the experimental spectrum (21), effective to provide an experimental spectrum having reduced background noise (39).

Figure 2:
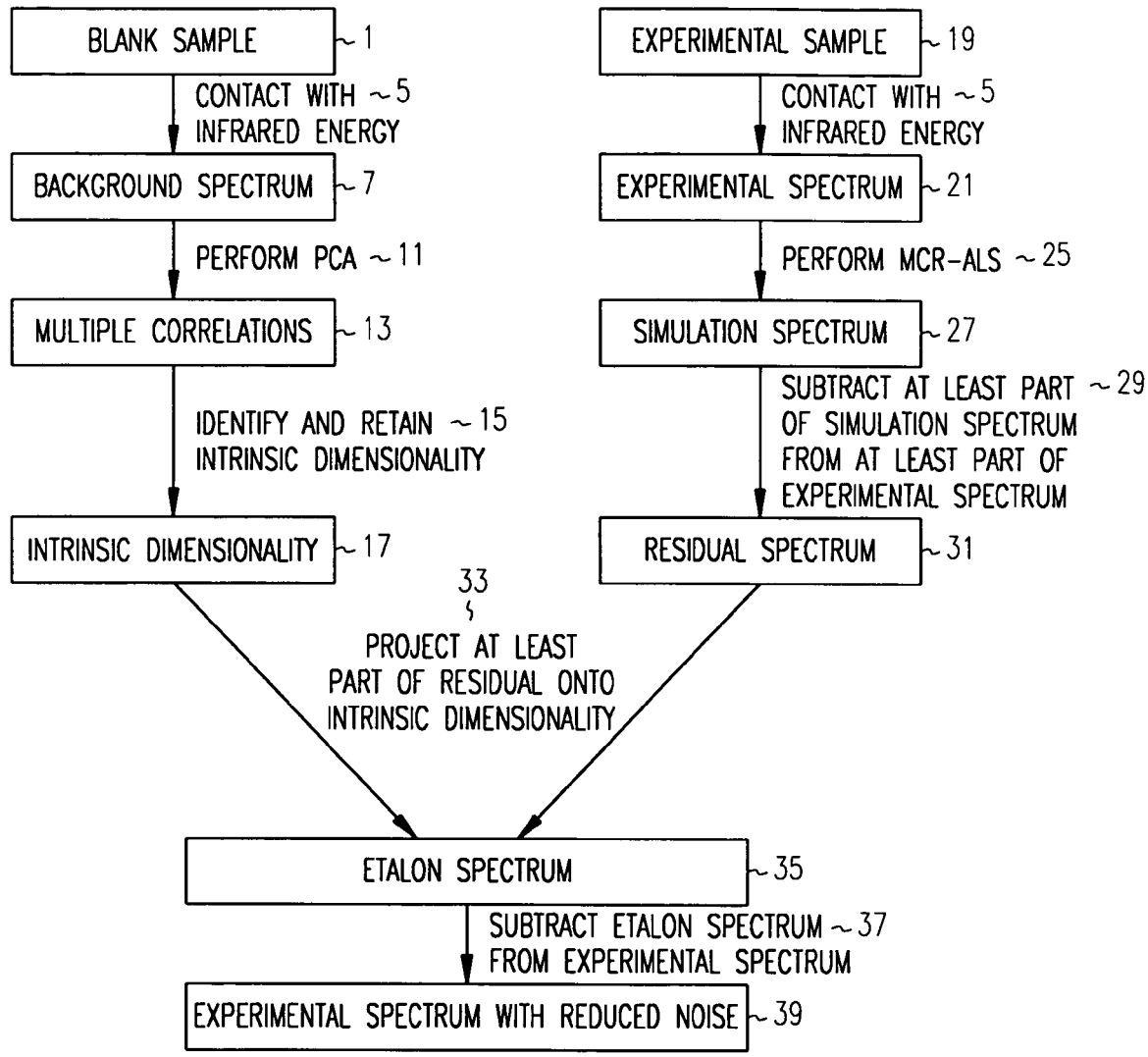
FIG. 2 illustrates a block flow diagram depicting the reduction of noise in a spectrum collected by infrared spectroscopy.

The embodiments of the present invention include a method to reduce background noise in an experimental absorbance spectrum (FIG. 2). A blank sample (1) can be contacted with infrared energy (5) sufficient to obtain a background spectrum (7). A principal component analysis (PCA) can be performed (11) on the background spectrum (7) sufficient to obtain multiple correlations (13) between variables in the background spectrum (7). The intrinsic dimensionality (17) of the background spectrum (7) can be identified and retained (15). An experimental sample (19) can be contacted with infrared energy (5) sufficient to obtain an experimental spectrum (21). A multivariate curve resolution-alternating least squares (MCR-ALS) analysis can be performed (25) on the experimental spectrum (21), based upon known characteristics of pure substances (19), effective to provide a simulation spectrum (27). At least part of the simulation spectrum (27) can be subtracted (29) from at least part of the experimental spectrum (21), effective to provide a residual spectrum (31). At least part of the residual spectrum (31) can be projected (33) onto the intrinsic dimensionality (17) of the background spectrum (7), effective to identify any etalons present in the residual spectrum (35). The etalon (35) can be removed (37) from the experimental spectrum (21), effective to provide an experimental spectrum having reduced background noise (39).

Figure 3:
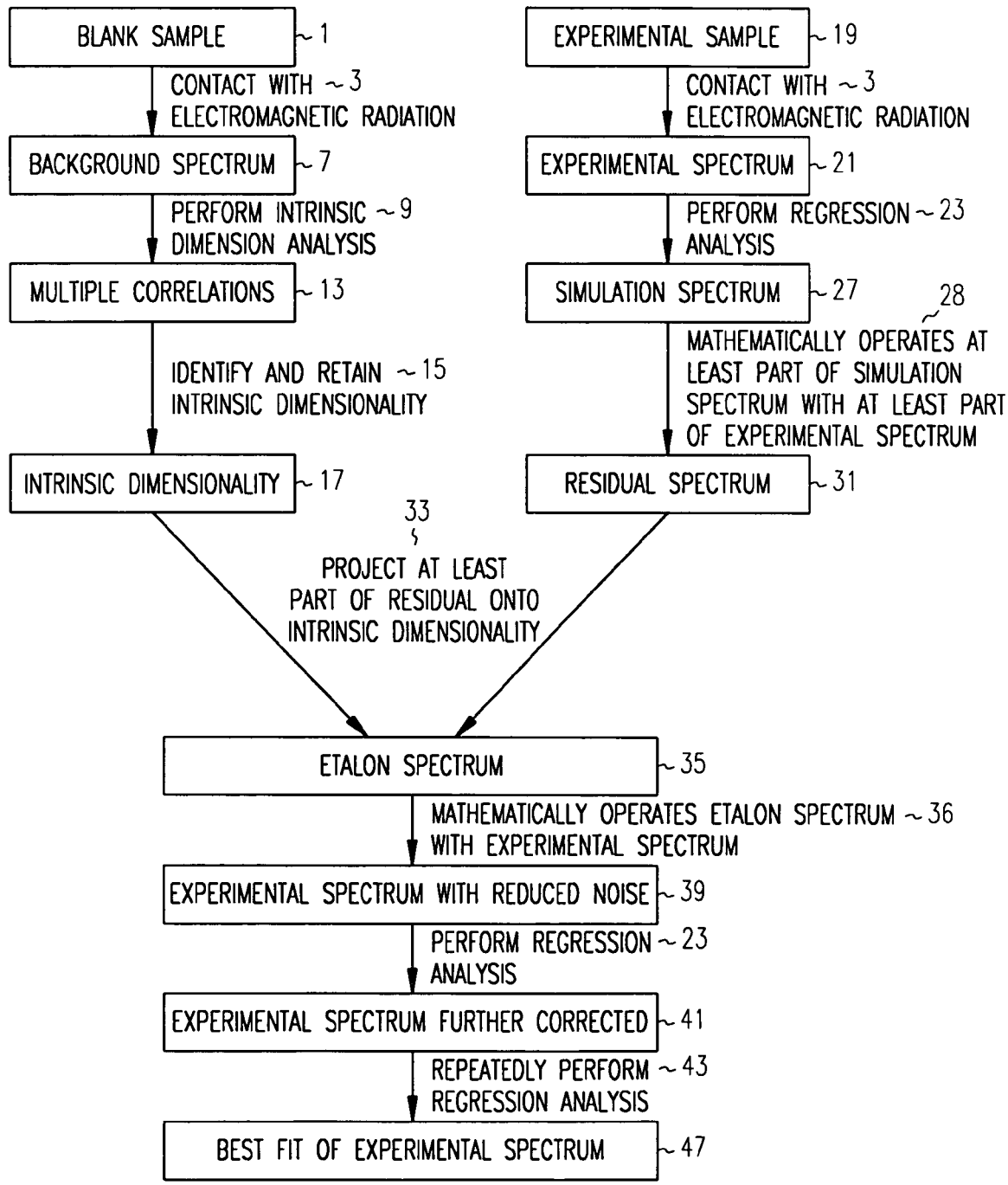
FIG. 3 illustrates a block flow diagram depicting the reduction of noise and subsequent refinement in a spectrum collected by spectroscopy.

The embodiments of the present invention include a method to reduce background noise in an experimental spectrum including refinement of the regression (FIG. 3). A blank sample (1) can be contacted with electromagnetic radiation (3) sufficient to obtain a background spectrum (7). An intrinsic dimension analysis can be performed (9) on the background spectrum (7) sufficient to obtain multiple correlations (13) between variables in the background spectrum (7). The intrinsic dimensionality (17) of the background spectrum (7) can be identified and retained (15). An experimental sample (19) can be contacted with electromagnetic radiation (3) sufficient to obtain an experimental spectrum (21). A regression analysis can be performed (23) on the experimental spectrum (21), based upon known characteristics of pure substances (19), effective to provide a simulation spectrum (27). At least part of the simulation spectrum (27) can be mathematically operated (28) with at least part of the experimental spectrum (21), effective to provide a residual spectrum (31). At least part of the residual spectrum (31) can be projected (33) onto the intrinsic dimensionality (17) of the background spectrum (7), effective to identify any etalons present in the residual spectrum (35). The etalon (35) can be mathematically operated (36) with the experimental spectrum (21), effective to provide an experimental spectrum having reduced background noise (39). A regression analysis (23) can be performed on the reduced noise experimental spectrum (39), effective to produce a further corrected experimental spectrum (41). The regression analysis can be repeatedly performed (43) until a best fit of the experimental spectrum (47) results.

Figure 4:
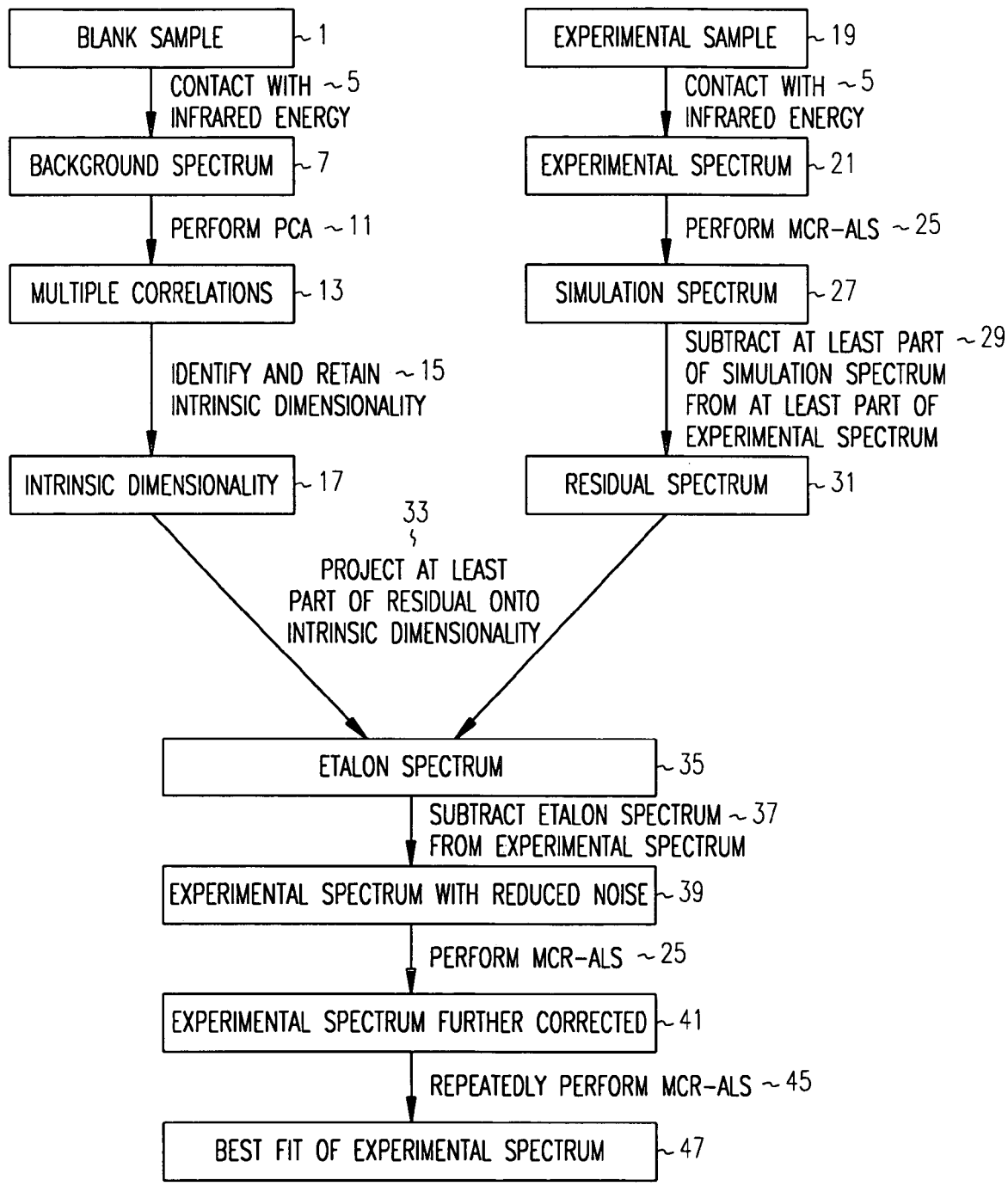
FIG. 4 illustrates a block flow diagram depicting the reduction of noise and subsequent refinement in a spectrum collected by infrared spectroscopy.

The embodiments of the present invention include a method to reduce background noise in an experimental absorbance spectrum including refinement of the regression (FIG. 4). A blank sample (1) can be contacted with infrared energy (5) sufficient to obtain a background spectrum (7). A principal component analysis (PCA) can be performed (11) on the background spectrum (7) sufficient to obtain multiple correlations (13) between variables in the background spectrum (7). The intrinsic dimensionality (17) of the background spectrum (7) can be identified and retained (15). An experimental sample (19) can be contacted with infrared energy (5) sufficient to obtain an experimental spectrum (21). A multivariate curve resolution-alternating least squares (MCR-ALS) analysis can be performed (25) on the experimental spectrum (21), based upon known characteristics of pure substances (19), effective to provide a simulation spectrum (27). At least part of the simulation spectrum (27) can be subtracted (29) from at least part of the experimental spectrum (21), effective to provide a residual spectrum (31). At least part of the residual spectrum (31) can be projected (33) onto the intrinsic dimensionality (17) of the background spectrum (7), effective to identify any etalons present in the residual spectrum (35). The etalon (35) can be removed (37) from the experimental spectrum (21), effective to provide an experimental spectrum having reduced background noise (39). A multivariate curve resolution-alternating least squares analysis (25) can be performed on the reduced noise experimental spectrum (39), effective to produce a further corrected experimental spectrum (41). The multivariate curve resolution-alternating least squares analysis can be repeatedly performed (45) until a best fit of the experimental spectrum (47) results.

Referring to FIGS. 1-4, methods to reduce background noise in an experimental spectrum are provided. The blank sample (1) used typically does not contain any amount of the target species. The cell or sample container could be subjected to a vacuum in order to remove interferences, but may not be necessary depending on the application and whether ambient air interacts with the source or target species. The sample container can fully or partially enclose the sample in a static position or the sample may also flow through a cell in an in-line or flow-through manner. Further, samples may be taken in any sample volume such as within an open space, tank, vessel, room or in the atmosphere. A spectroscopic device, which may be more specifically a laser spectroscopic device, contacts the blank sample (1) with electromagnetic radiation (3). The spectroscopic device may be in a laboratory, in the field, mounted or carried on a car, train or industrial equipment, for example. The electromagnetic radiation (3) can be infrared energy (5), which may include wavelength ranges in mid-infrared or near-infrared.

The spectroscopic device computes a background spectrum (7) as a result of the electromagnetic radiation source interacting with any species or electromagnetic effects in its path. The background spectrum (7) will typically consist of only noise. An intrinsic dimensionality analysis can be performed (9) on the background spectrum. For example, more specifically, principal component analysis (PCA) (11), singular value decomposition (SVD), eigenfactor analysis, neural networks, pattern recognition technique, techniques that determine intrinsic dimensionality or wavelet analysis can be performed in order to identify the existence of multiple correlations in the data. The intrinsic dimension analysis methods are known statistical procedures used to identify and rank the relationships between variables in a data set. In a spectrum, those variables may be concentrations of sample and interferents, absorbance intensity, wavelength range, component structure, inter-molecular attractions and distortions, among others. The intrinsic dimensionality analysis methods can describe these multiple correlations (13) by way of vectors and numerical values. Statistical selection rules can be used to identify which correlations are insignificant and can, therefore, be discarded for the analysis. The intrinsic dimensionality (17) can be retained. More specifically, those correlations that include the strongest characterize the intrinsic dimensionality of the variables. One of the advantages of the embodiments of the invention is that the intrinsic dimensionality of the background spectrum can be calculated and prepared independently of the collection of experimental data. Unlike traditional methods, embodiments of the present invention may allow etalon characterization to be performed in a single pass or scan and do not require time consuming background scans performed before and possibly after collection of experimental data which may take considerably more time.

A spectroscopic device, which may be more specifically a laser spectroscopic device, contacts an experimental sample (19) containing the target species with electromagnetic radiation (3). More specifically, the electromagnetic radiation (3) can be infrared energy (5), which may include wavelength ranges in mid-infrared or near-infrared. The experimental sample (19) may be enclosed in a static cell or flowing in-line.

The spectroscopic device computes an experimental spectrum (21) as a result of the electromagnetic radiation (3) source interacting with the target species, interferents and any optical effects in its path. The experimental spectrum is made up of spectral characteristics unique to the target species, but can also contain misleading information caused by undesirable noise and other effects.

A regression analysis can be performed (23) on the experimental spectrum (21). For example, more specifically, multivariate curve resolution-alternating least squares (MCR-ALS) (25), principal component regression, partial least squares, projection of latent structures, linear least squares, solution of simultaneous equations, non-linear least squares, linear regression or non-linear regression can be applied. The regression analysis (23) uses known characteristics of pure substances that may be present in the experimental sample (19) to create a simulation spectrum (27). More specifically, pure substances have unique spectral features that are used to create a simulation spectrum (27). The pure substance spectra make up a library of reference spectra and corresponding reference points that can be utilized manually or via software to create a simulation spectrum (27). The pure substances may be used as a baseline and may be made up of multiple known components, such as an uncontaminated hydrocarbon mixture from a refinery which does not vary over the relevant duration and is locally homogeneous.

At least part of the simulation spectrum (27) can be mathematically operated (28) with at least part of the experimental spectrum (21), producing a residual spectrum (31). At least part of the residual spectrum (31) can be projected (33) onto the intrinsic dimensionality (17), effective to identify those etalon patterns that are present in the residual spectrum (31). The resulting projection produces an etalon spectrum (35).

The etalon spectrum (35) can be mathematically operated (36) with the experimental spectrum (21) to produce an experimental spectrum with reduced noise (39). Optionally, a regression analysis (23) could be further performed on the experimental spectrum with reduced noise (39). For example, more specifically, a multivariate curve resolution-alternating least squares (MCR-ALS) analysis could be performed. The result would then be an experimental spectrum further corrected (41). The regression analysis could be repeatedly performed (43) until a best fit of experimental spectrum (47) is found. For example, more specifically, MCR-ALS could be repeatedly performed (45). The best fit of the experimental spectrum would be determined by using a statistical method to determine that the subsequent difference between the spectra has become numerically insignificant.

Figure 5:
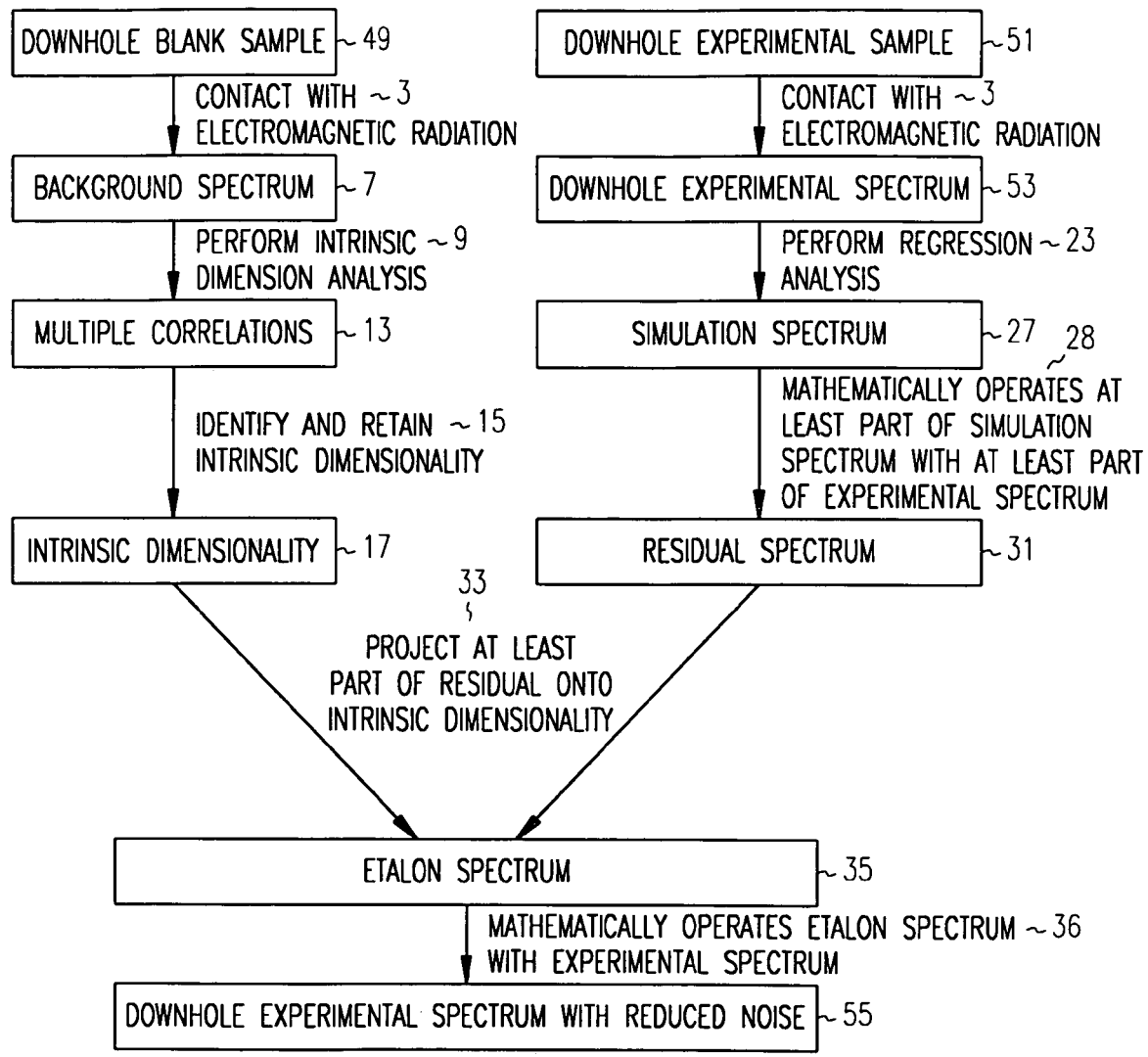
FIG. 5 illustrates a block flow diagram depicting the reduction of noise in a spectrum collected by spectroscopy downhole.

Referring to FIGS. 5-10, novel methods to reduce background noise in an experimental spectrum are provided for various industries as examples of possible applications. The embodiments of the present invention include a method to reduce background noise in an experimental spectrum downhole in the oil services industry (FIG. 5). A downhole blank sample (49) can be contacted with electromagnetic radiation (3) sufficient to obtain a background spectrum (7). An intrinsic dimension analysis can be performed (9) on the background spectrum (7) sufficient to obtain multiple correlations (13) between variables in the background spectrum (7). The intrinsic dimensionality (17) of the background spectrum (7) can be identified and retained (15). A downhole experimental sample (51) can be contacted with electromagnetic radiation (3) sufficient to obtain a downhole experimental spectrum (53). A regression analysis can be performed (23) on the downhole experimental spectrum (53), based upon known characteristics of pure substances (51), effective to provide a simulation spectrum (27). At least part of the simulation spectrum (27) can be mathematically operated (28) with at least part of the downhole experimental spectrum (53), effective to provide a residual spectrum (31). At least part of the residual spectrum (31) can be projected (33) onto the intrinsic dimensionality (17) of the background spectrum (7), effective to identify any etalons present in the residual spectrum (35). The etalon (35) can be mathematically operated (36) with the downhole experimental spectrum (53), effective to provide a downhole experimental spectrum having reduced background noise (55).

Figure 6:
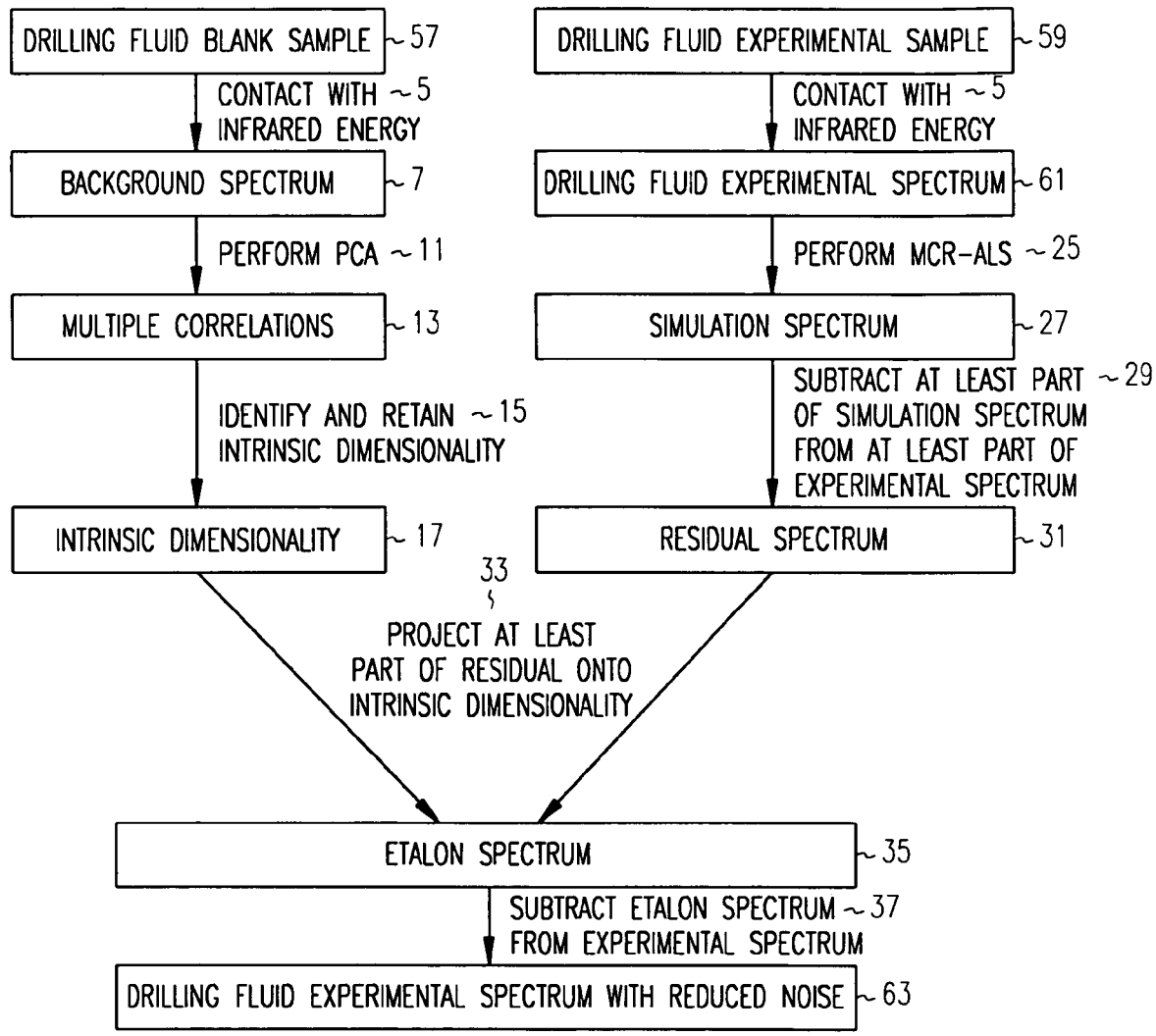
FIG. 6 illustrates a block flow diagram depicting the reduction of noise in a drilling fluid spectrum collected by infrared spectroscopy.

The embodiments of the present invention include a method to reduce background noise in a drilling fluid experimental absorbance spectrum (FIG. 6). A drilling fluid blank sample (57) can be contacted with infrared energy (5) sufficient to obtain a background spectrum (7). A principal component analysis (PCA) can be performed (11) on the background spectrum (7) sufficient to obtain multiple correlations (13) between variables in the background spectrum (7). The intrinsic dimensionality (17) of the background spectrum (7) can be identified and retained (15). A drilling fluid experimental sample (59) can be contacted with infrared energy (5) sufficient to obtain a drilling fluid experimental spectrum (61). A multivariate curve resolution-alternating least squares (MCR-ALS) analysis can be performed (25) on the drilling fluid experimental spectrum (61), based upon known characteristics of pure substances (59), effective to provide a simulation spectrum (27). At least part of the simulation spectrum (27) can be subtracted (29) from at least part of the drilling fluid experimental spectrum (61), effective to provide a residual spectrum (31). At least part of the residual spectrum (31) can be projected (33) onto the intrinsic dimensionality (17) of the background spectrum (7), effective to identify any etalons present in the residual spectrum (35). The etalon (35) can be removed (37) from the drilling fluid experimental spectrum (61), effective to provide a drilling fluid experimental spectrum having reduced background noise (63).

In reference to FIGS. 5-6, there may be many possible applications of the present embodiments of the invention to the oil services industry. Samples collected downhole may be analyzed to determine the quality of oil, unique properties of the oil for characterization and for geo-steering purposes. Examples of sampling may include drilling fluid, downhole gases, oil, formation fluids and cuttings. More specifically for example, spectrometers used for sampling may be mounted on machinery located downhole or used on site or in the laboratory. Spectrometers mounted downhole or at the surface would have the ability to analyze a flowing sample in real time as well as analyze samples collected intermittently. The reduction of noise in experimental spectra, coupled with significantly increased speed and method simplicity allow for immediate benefits in the oil services industry.

Figure 7:
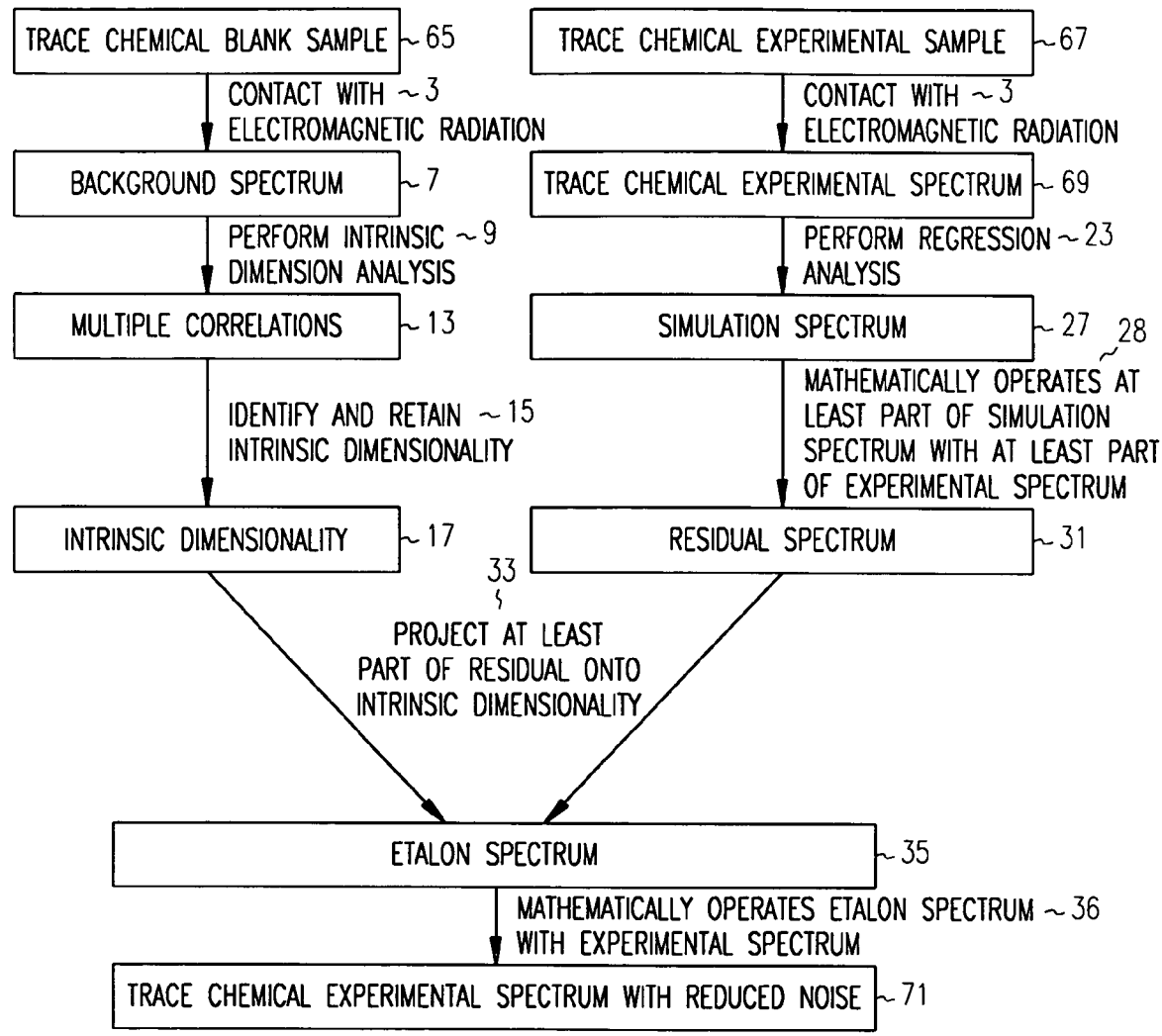
FIG. 7 illustrates a block flow diagram depicting the reduction of noise in a trace chemical spectrum collected by spectroscopy.

The embodiments of the present invention include a method to reduce background noise in an experimental spectrum in the field of environmental testing (FIG. 7). A trace chemical blank sample (65) can be contacted with electromagnetic radiation (3) sufficient to obtain a background spectrum (7). An intrinsic dimension analysis can be performed (9) on the background spectrum (7) sufficient to obtain multiple correlations (13) between variables in the background spectrum (7). The intrinsic dimensionality (17) of the background spectrum (7) can be identified and retained (15). A trace chemical experimental sample (67) can be contacted with electromagnetic radiation (3) sufficient to obtain a trace chemical experimental spectrum (69). A regression analysis can be performed (23) on the trace chemical experimental spectrum (69), based upon known characteristics of pure substances (67), effective to provide a simulation spectrum (27). At least part of the simulation spectrum (27) can be mathematically operated (28) with at least part of the trace chemical experimental spectrum (69), effective to provide a residual spectrum (31). At least part of the residual spectrum (31) can be projected (33) onto the intrinsic dimensionality (17) of the background spectrum (7), effective to identify any etalons present in the residual spectrum (35). The etalon (35) can be mathematically operated (36) with the trace chemical experimental spectrum (69), effective to provide a trace chemical experimental spectrum having reduced background noise (71).

Figure 8:
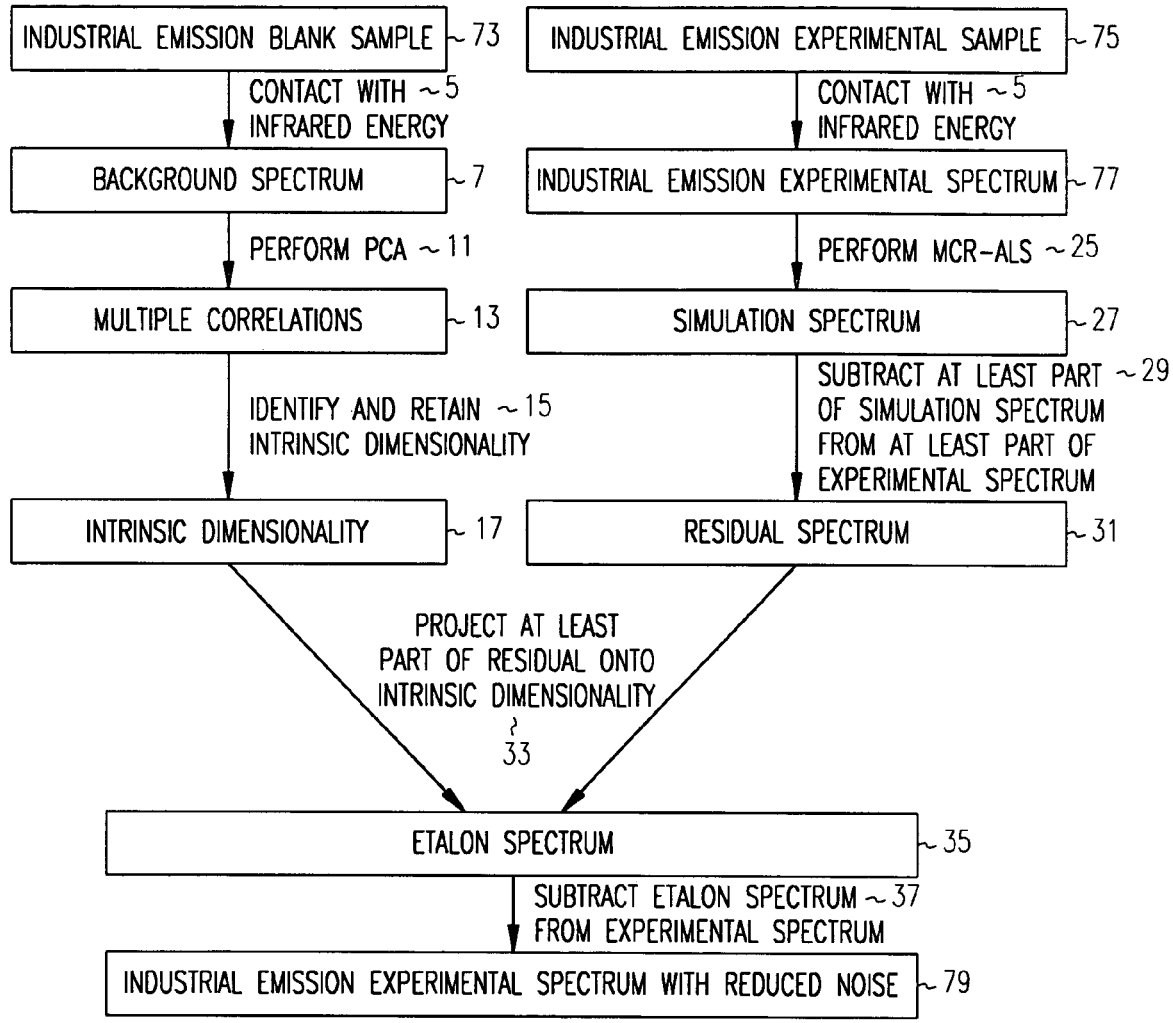
FIG. 8 illustrates a block flow diagram depicting the reduction of noise in an industrial emission spectrum collected by infrared spectroscopy.

The embodiments of the present invention include a method to reduce background noise in an industrial emission experimental absorbance spectrum (FIG. 8). An industrial emission blank sample (73) can be contacted with infrared energy (5) sufficient to obtain a background spectrum (7). A principal component analysis (PCA) can be performed (11) on the background spectrum (7) sufficient to obtain multiple correlations (13) between variables in the background spectrum (7). The intrinsic dimensionality (17) of the background spectrum (7) can be identified and retained (15). An industrial emission experimental sample (75) can be contacted with infrared energy (5) sufficient to obtain an industrial emission experimental spectrum (77). A multivariate curve resolution-alternating least squares (MCR-ALS) analysis can be performed (25) on the industrial emission experimental spectrum (77), based upon known characteristics of pure substances (75), effective to provide a simulation spectrum (27). At least part of the simulation spectrum (27) can be subtracted (29) from at least part of the industrial emission experimental spectrum (77), effective to provide a residual spectrum (31). At least part of the residual spectrum (31) can be projected (33) onto the intrinsic dimensionality (17) of the background spectrum (7), effective to identify any etalons present in the residual spectrum (35). The etalon (35) can be removed (37) from the industrial emission experimental spectrum (77), effective to provide an industrial emission experimental spectrum having reduced background noise (79).

In reference to FIGS. 7-8, embodiments of the present invention may be applied to the field of environmental testing. Because one of the advantages of the embodiments of the present invention is to significantly reduce noise in an experimental spectrum, the detection and quantification of trace chemicals in the environment can be performed at a level not possible before. Spectrometers may read samples collected from soil, water and air. Samples may be collected and analyzed in real time at such places as industrial complexes and treatment plants. Due to the threat of global pollution, composition of air and water samples may be chemically characterized in order to identify the sources of pollution. The quality of emissions analysis in manufacturing and processing plants may be increased due to the effectiveness of the current embodiments of the invention.

Figure 9:
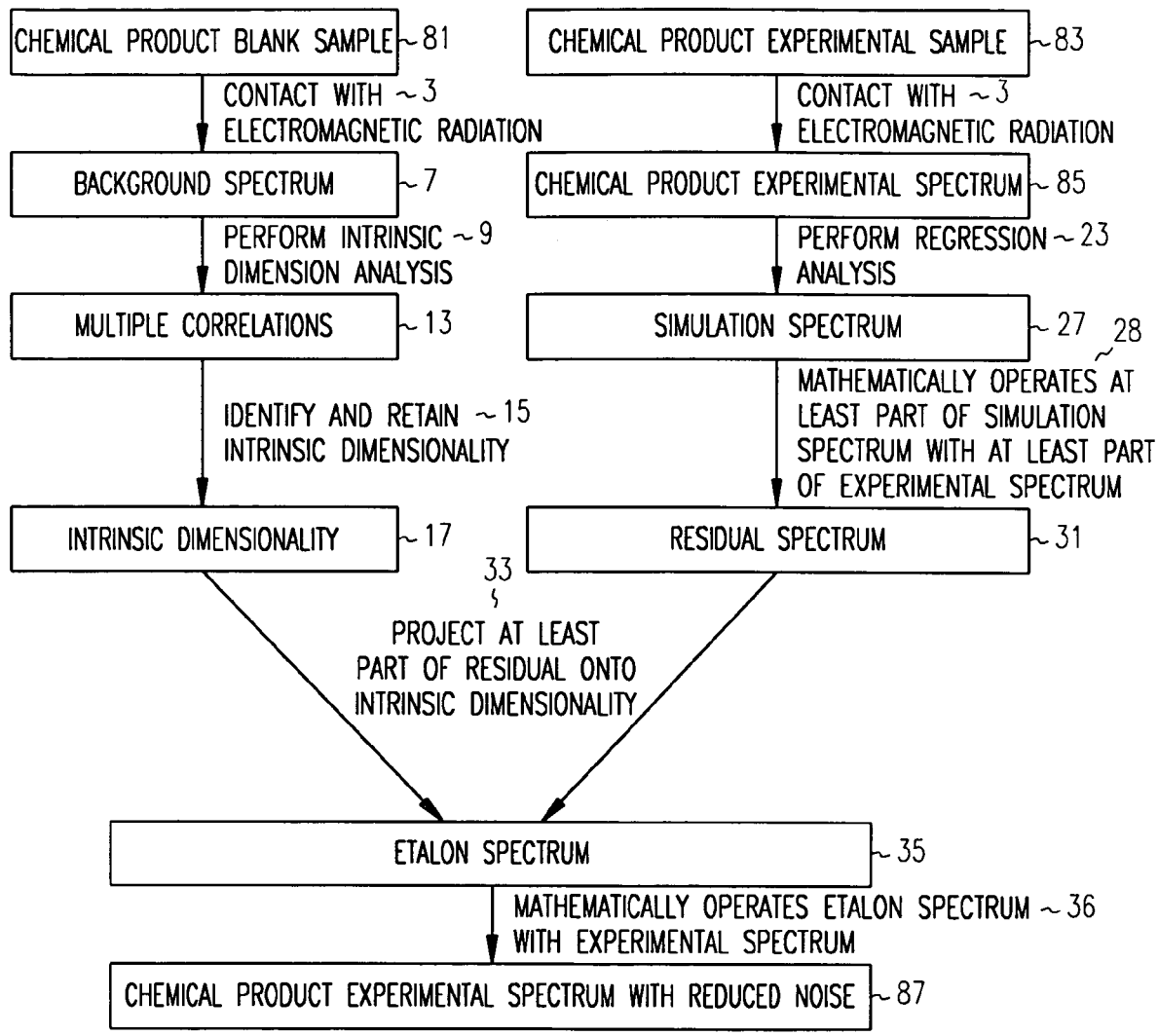
FIG. 9 illustrates a block flow diagram depicting the reduction of noise in a chemical product spectrum collected by spectroscopy.

The embodiments of the present invention include a method to reduce background noise in an experimental spectrum in the field of quality control (FIG. 9). A chemical product blank sample (81) can be contacted with electromagnetic radiation (3) sufficient to obtain a background spectrum (7). An intrinsic dimension analysis can be performed (9) on the background spectrum (7) sufficient to obtain multiple correlations (13) between variables in the background spectrum (7). The intrinsic dimensionality (17) of the background spectrum (7) can be identified and retained (15). A chemical product experimental sample (83) can be contacted with electromagnetic radiation (3) sufficient to obtain a chemical product experimental spectrum (85). A regression analysis can be performed (23) on the chemical product experimental spectrum (85), based upon known characteristics of pure substances (83), effective to provide a simulation spectrum (27). At least part of the simulation spectrum (27) can be mathematically operated (28) with at least part of the chemical product experimental spectrum (85), effective to provide a residual spectrum (31). At least part of the residual spectrum (31) can be projected (33) onto the intrinsic dimensionality (17) of the background spectrum (7), effective to identify any etalons present in the residual spectrum (35). The etalon (35) can be mathematically operated (36) with the chemical product experimental spectrum (85), effective to provide a chemical product experimental spectrum having reduced background noise (87).

Figure 10:
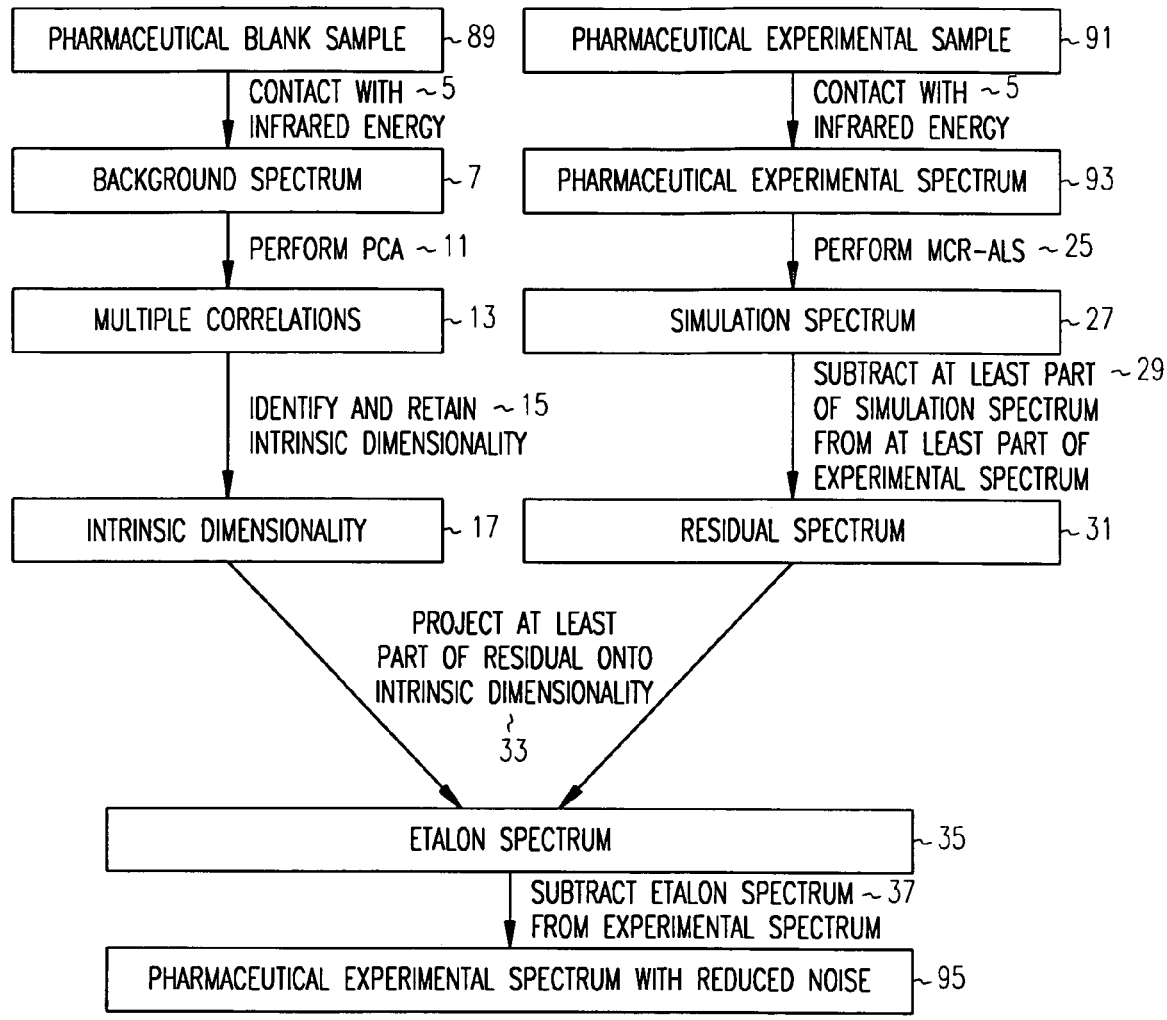
FIG. 10 illustrates a block flow diagram depicting the reduction of in a pharmaceutical spectrum collected by infrared spectroscopy.

The embodiments of the present invention include a method to reduce background noise in a pharmaceutical experimental absorbance spectrum (FIG. 10). A pharmaceutical blank sample (89) can be contacted with infrared energy (5) sufficient to obtain a background spectrum (7). A principal component analysis (PCA) can be performed (11) on the background spectrum (7) sufficient to obtain multiple correlations (13) between variables in the background spectrum (7). The intrinsic dimensionality (17) of the background spectrum (7) can be identified and retained (15). A pharmaceutical experimental sample (91) can be contacted with infrared energy (5) sufficient to obtain a pharmaceutical experimental spectrum (93). A multivariate curve resolution-alternating least squares (MCR-ALS) analysis can be performed (25) on the pharmaceutical experimental spectrum (93), based upon known characteristics of pure substances (91), effective to provide a simulation spectrum (27). At least part of the simulation spectrum (27) can be subtracted (29) from at least part of the pharmaceutical experimental spectrum (93), effective to provide a residual spectrum (31). At least part of the residual spectrum (31) can be projected (33) onto the intrinsic dimensionality (17) of the background spectrum (7), effective to identify any etalons present in the residual spectrum (35). The etalon (35) can be removed (37) from the pharmaceutical experimental spectrum (93), effective to provide an pharmaceutical experimental spectrum having reduced background noise (95).

In reference to FIGS. 9-10, embodiments of the present invention may be applied to the quality control, field. By reducing the amount of noise in a spectrum collected by a spectroscopy, the detection of impurities in a chemical product batch for the purpose of quality control may be significantly enhanced. Embodiments of the present invention allow for detection of undesirable species in-line, without disrupting the chemical product manufacturing process. Embodiments of the present invention may be used in the pharmaceutical industry to detect such species as un-reacted reagents or contamination. The quality of chemical products and safety of pharmaceuticals may be positively influenced.

Figure 16:
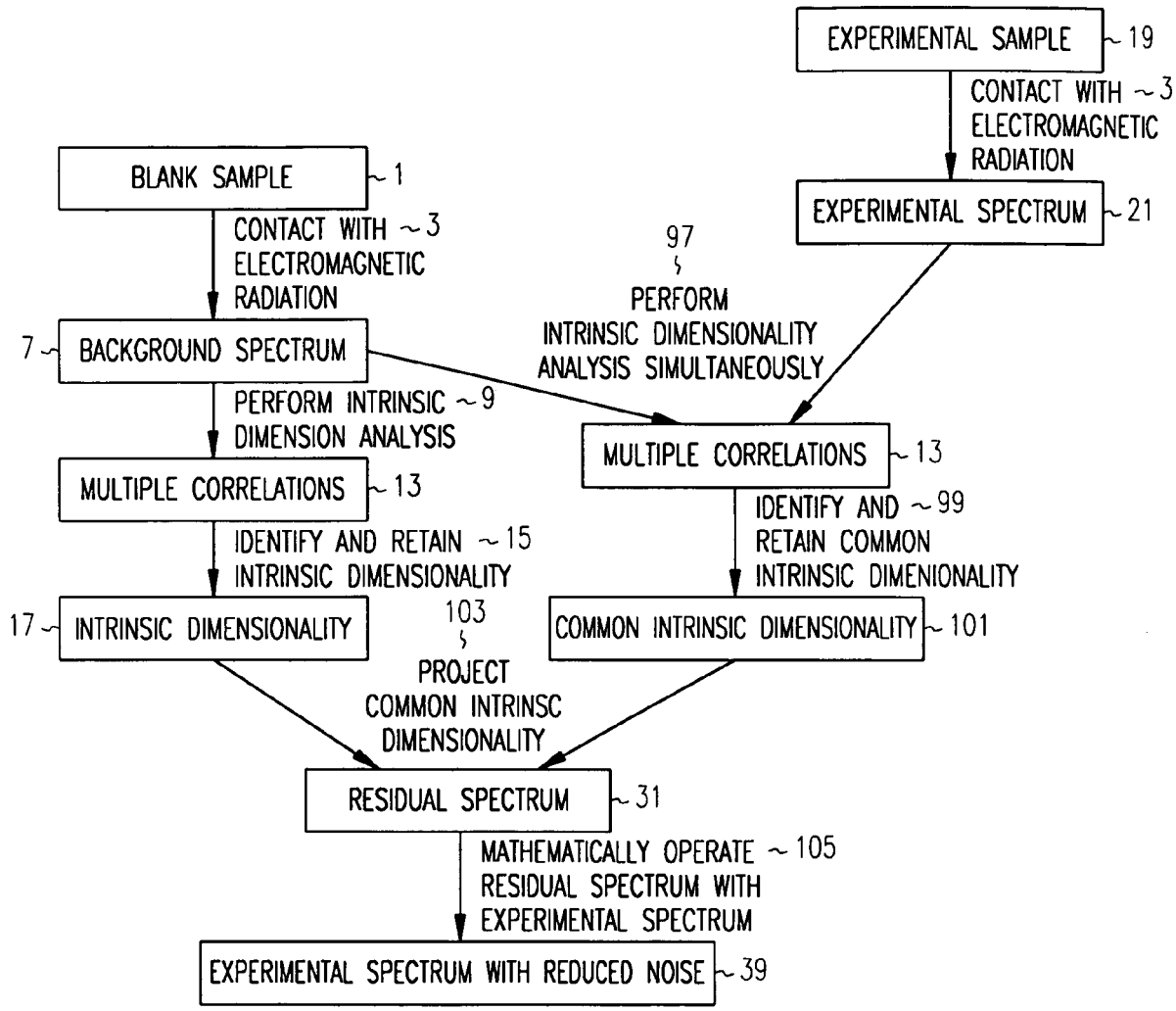
FIG. 16 illustrates a block flow diagram depicting an embodiment of the invention to reduce the noise in a spectrum collected by spectroscopy.

The embodiments of the present invention include a method to reduce background noise in a spectrum without relying on a simulation spectrum (FIG. 16). A blank sample (1) can be contacted with electromagnetic radiation (3) sufficient to obtain a background spectrum (7). An intrinsic dimension analysis can be performed (9) on the background spectrum (7) sufficient to obtain multiple correlations (13) between variables in the background spectrum (7). The intrinsic dimensionality (17) of the background spectrum (7) can be identified and retained (15). An experimental sample (19) can be contacted with electromagnetic radiation (3) sufficient to obtain an experimental spectrum (21). An intrinsic dimension analysis may be performed simultaneously (97) on the background spectrum (7) and experimental spectrum (21) sufficient to obtain multiple correlations (13) between variables in the background spectrum (7) and experimental spectrum (21). The common intrinsic dimensionality (101) of the background spectrum (7) and experimental spectrum (21) can be identified and retained (99). The common intrinsic dimensionality (101) may be projected (103) onto the intrinsic dimensionality (17) of the background spectrum (7) sufficient to produce a residual spectrum (31). The residual spectrum (31) may be mathematically operated (105) with the experimental spectrum (21) to obtain an experimental spectrum with reduced noise (39).

The embodiments of the present invention include a method to reduce background noise in a spectrum without relying on a simulation spectrum (FIG. 17) and includes the steps of further iterations. A blank sample (1) can be contacted with electromagnetic radiation (3) sufficient to obtain a background spectrum (7). An intrinsic dimension analysis can be performed (9) on the background spectrum (7) sufficient to obtain multiple correlations (13) between variables in the background spectrum (7). The intrinsic dimensionality (17) of the background spectrum (7) can be identified and retained (15). An experimental sample (19) can be contacted with electromagnetic radiation (3) sufficient to obtain an experimental spectrum (21). An intrinsic dimension analysis may be performed simultaneously (97) on the background spectrum (7) and experimental spectrum (21) sufficient to obtain multiple correlations (13) between variables in the background spectrum (7) and experimental spectrum (21). The common intrinsic dimensionality (101) of the background spectrum (7) and experimental spectrum (21) can be identified and retained (99). The common intrinsic dimensionality (101) may be projected (103) onto the intrinsic dimensionality (17) of the background spectrum (7) sufficient to produce a residual spectrum (31). An intrinsic dimension analysis may be performed simultaneously (97) on the background spectrum (7) and residual spectrum (31) sufficient to obtain multiple correlations (13) between variables in the background spectrum (7) and residual spectrum (31). The common intrinsic dimensionality (101) of the background spectrum (7) and residual spectrum (31) can be identified and retained (99). The common intrinsic dimensionality (101) may be re-projected (107) onto the intrinsic dimensionality (17) of the background spectrum (7) sufficient to produce a second residual spectrum (109). The second residual spectrum (109) may be mathematically operated (111) with the experimental spectrum (21) to obtain an experimental spectrum with reduced noise (39).

Figure 17:
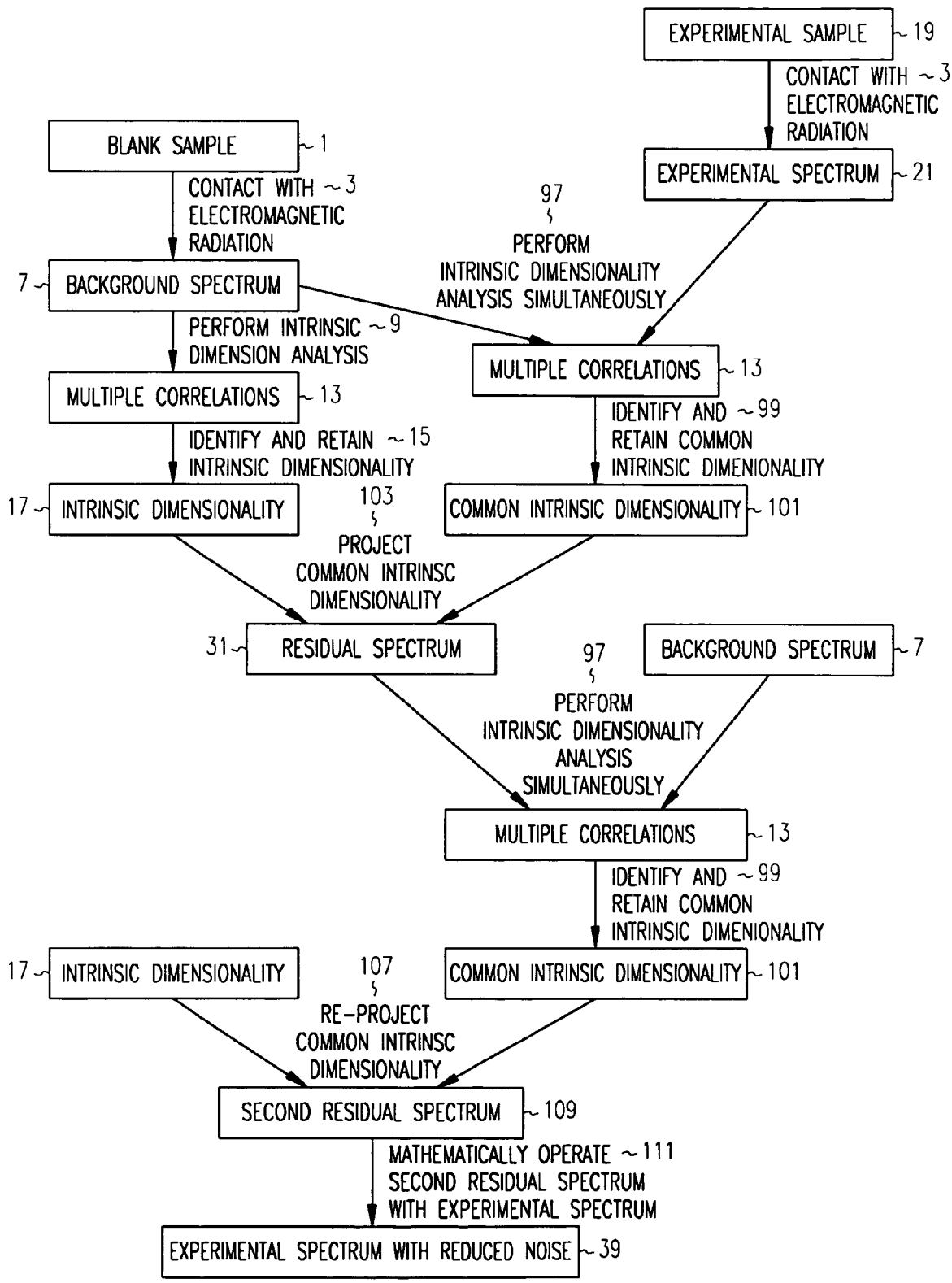
FIG. 17 illustrates a block flow diagram depicting a further embodiment of the invention to reduce the noise in a spectrum collected by spectroscopy.

Referring to FIGS. 16-17, methods to reduce background noise in an experimental spectrum are provided without relying on a simulation spectrum. FIG. 16 illustrates a modification and further embodiment of the disclosed method to reduce background noise in a spectrum. The advantage of the method focuses on the reduction of etalon noise in a spectrum without the use of spectral features from pure substances used as a simulation spectrum. The steps used in previously mentioned embodiments of the invention discuss the use of a simulation spectrum in creating a residual spectrum. The simulation spectrum is made from the know spectral characteristics of pure substances. The current embodiment of the invention bypasses such steps by simultaneously performing an intrinsic dimension analysis on the background and experimental spectra and comparing the resulting common intrinsic dimensionality to the independently identified intrinsic dimensionality of the background spectrum alone. The resulting residual spectrum may be mathematically operated with the experimental spectrum in order to reduce noise. By reducing noise in an experimental spectrum without using a simulation spectrum, a greater accuracy may be achieved by not relying on a model that could potentially contain misrepresentations in relation to the target sample. FIG. 17 represents a method to further iterate the results of FIG. 16. The reiteration of the residual spectrum allows for a further refinement of the intrinsic dimensionality of the background spectrum. The second residual spectrum is then used to produce an experimental spectrum with reduced noise. The process can be repeated as many times as needed to further reduce the noise in a spectrum.

One suitable apparatus useful for carrying out embodiments of the present invention is described, e.g., in U.S. Patent Application Number 20040164237, filed on Mar. 1, 2004, published on Aug. 26, 2004, assigned to Halliburton Energy Services, Inc. The contents of U.S. Patent Application Number 20040164237 are incorporated by reference herein in its entirety. The application relates to a method and apparatus for providing real-time data indicative of the isotopic composition of formation fluids during drilling. The method includes the steps of: providing a reference fluid having a known isotopic composition in a reference cell; capturing a sample of formation; providing at least one laser beam; passing a beam through the reference fluid, measuring the reference-measurement beam before and after it passes through the reference fluid; and passing a beam through the sample, measuring the beam before and after it passes through the sample, and calculating a first isotope concentration from those measurements. The measurements can provide information relating to the carbon isotopic composition of individual compounds in hydrocarbon gas mixtures, with the individual compounds including methane, ethane, propane, iso- or normal butane, or iso- or normal pentane.

EXAMPLES

Figure 11A:
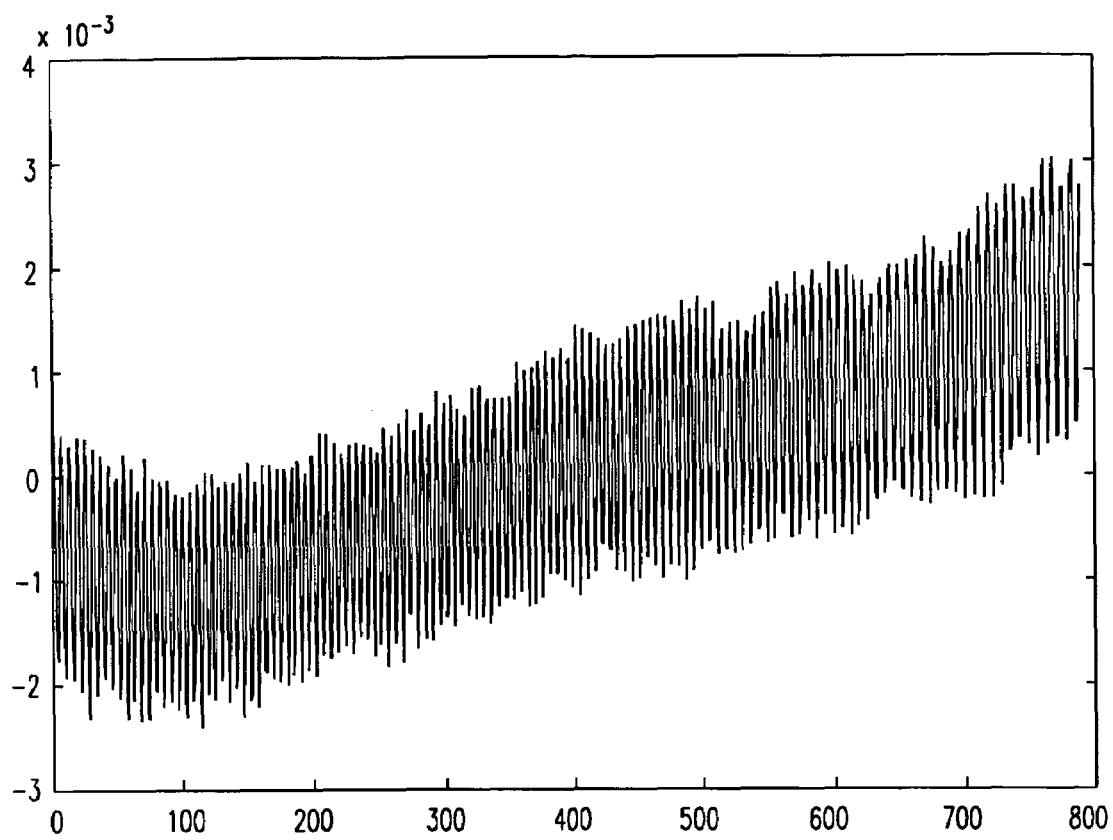
FIG. 11*a* illustrates a graph depicting an actual background.
Figure 11B:
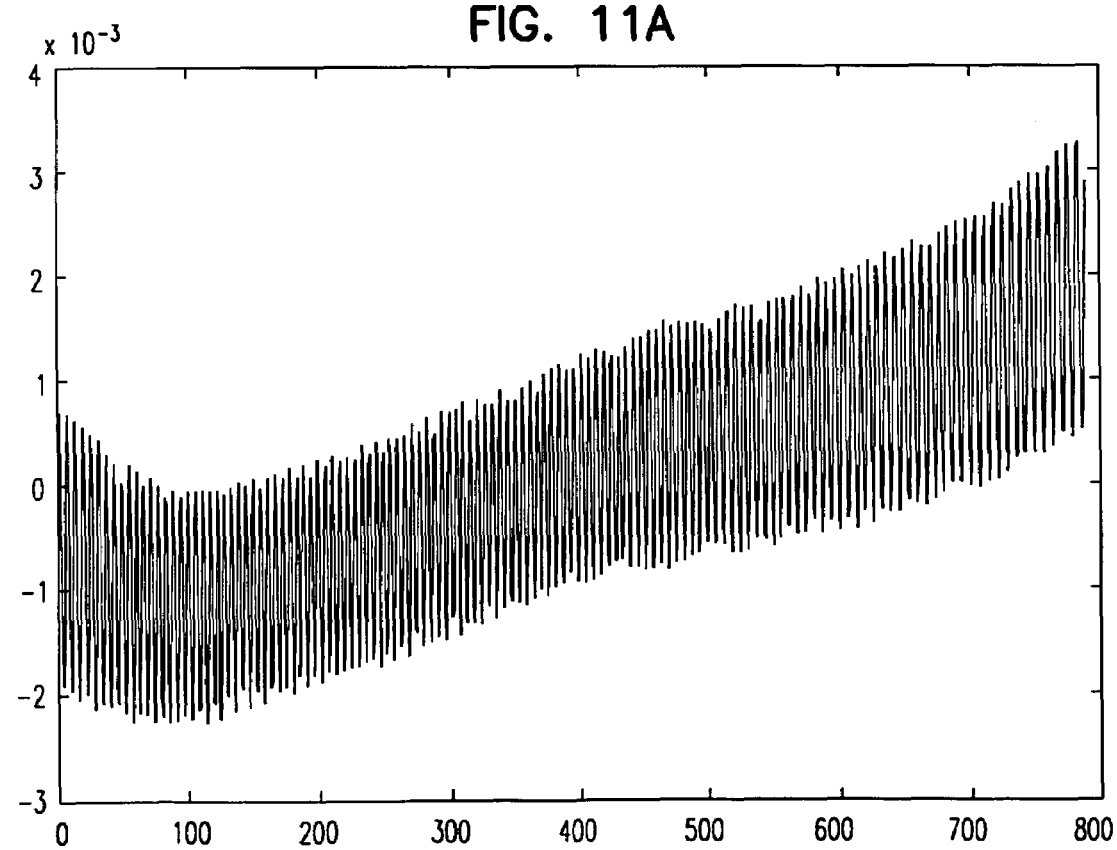
FIG. 11*b* illustrates a graph depicting a simulation background.
Figure 11C:
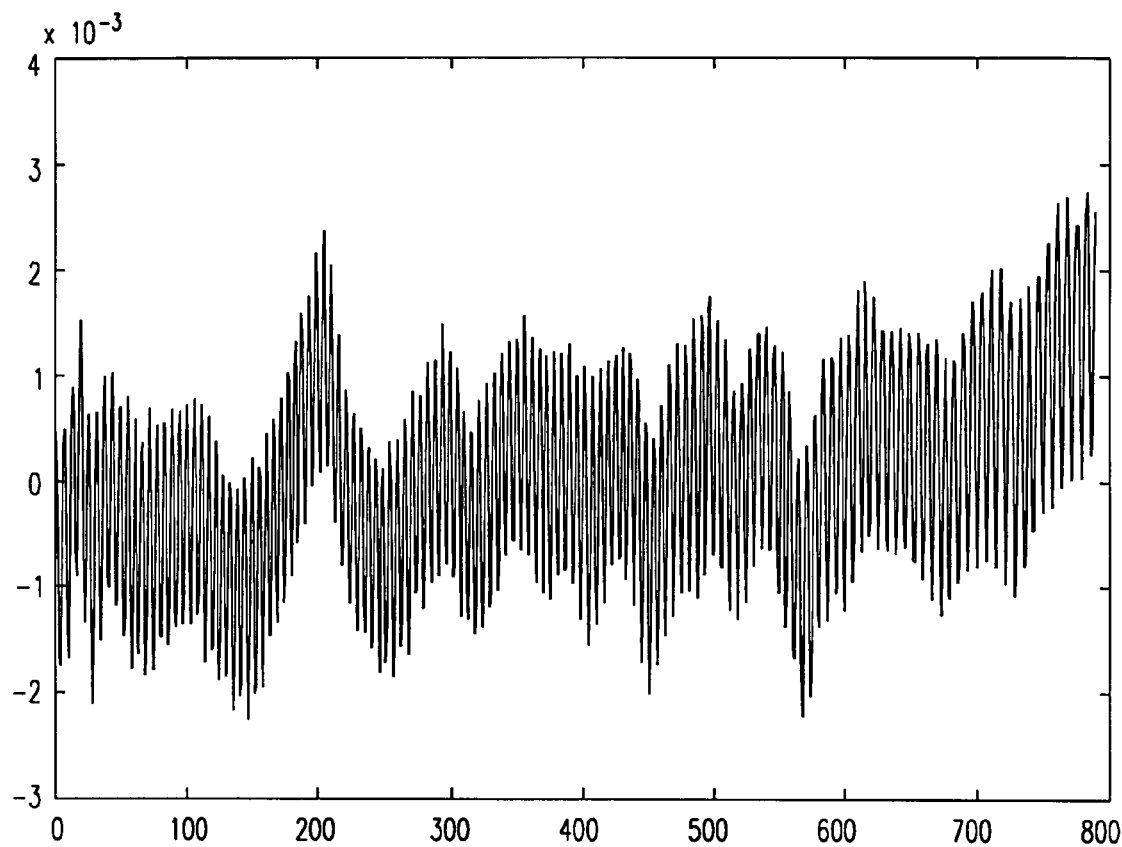
FIG. 11*c* illustrates a graph depicting a residual.
Figure 11D:
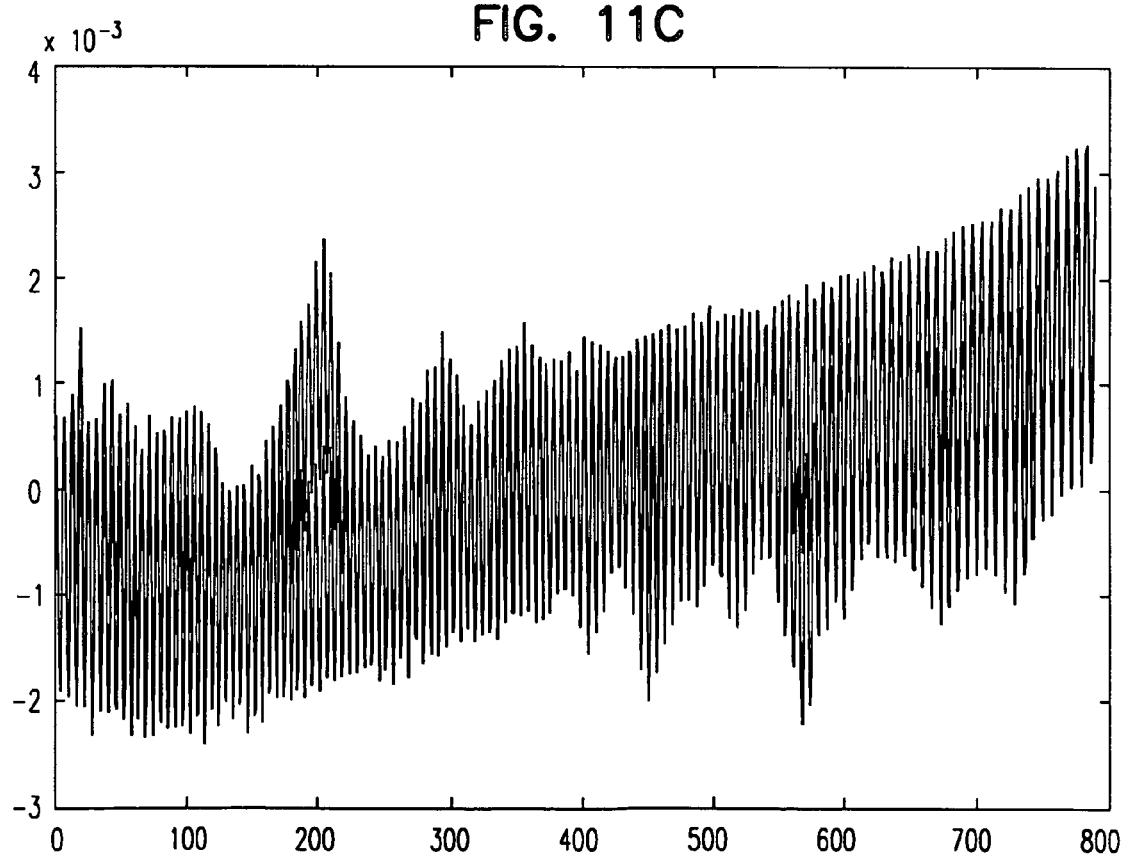
FIG. 11*d* illustrates a graph depicting an actual background, a simulation background and a residual.
Figure 12A:
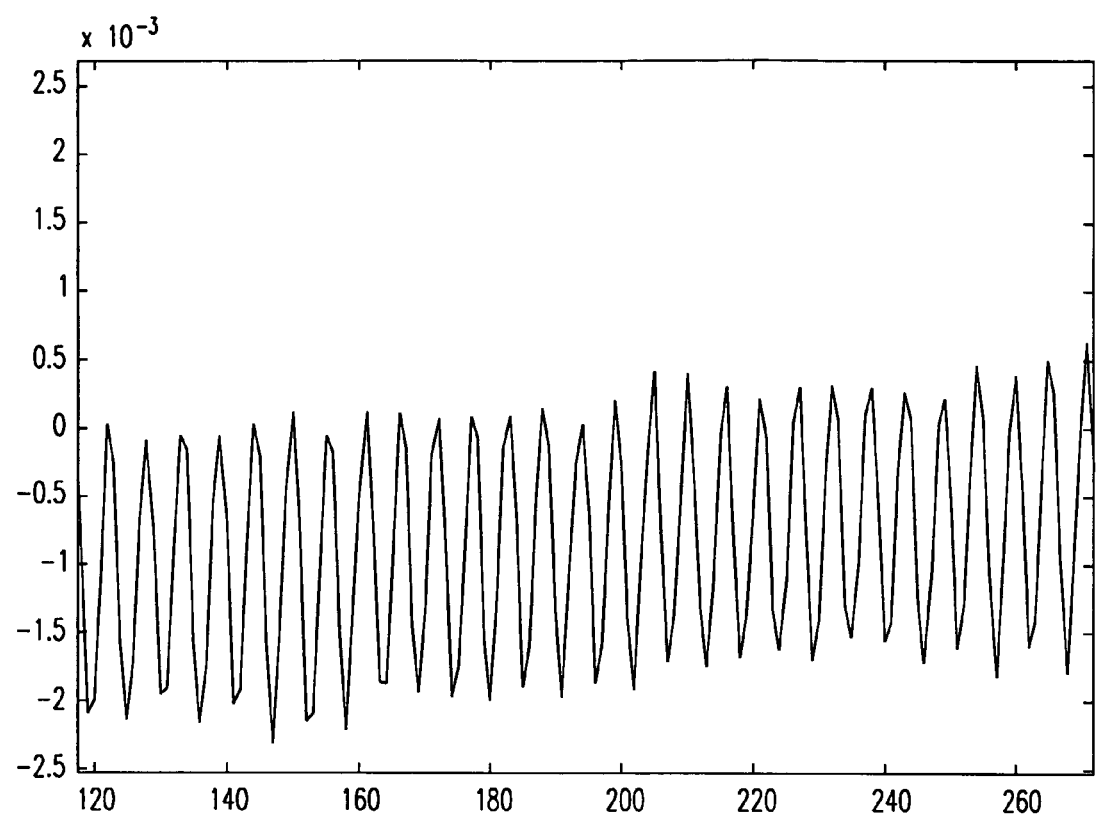
FIG. 12*a* illustrates a graph depicting a zoomed in picture of FIG. 11*a*.
Figure 12B:
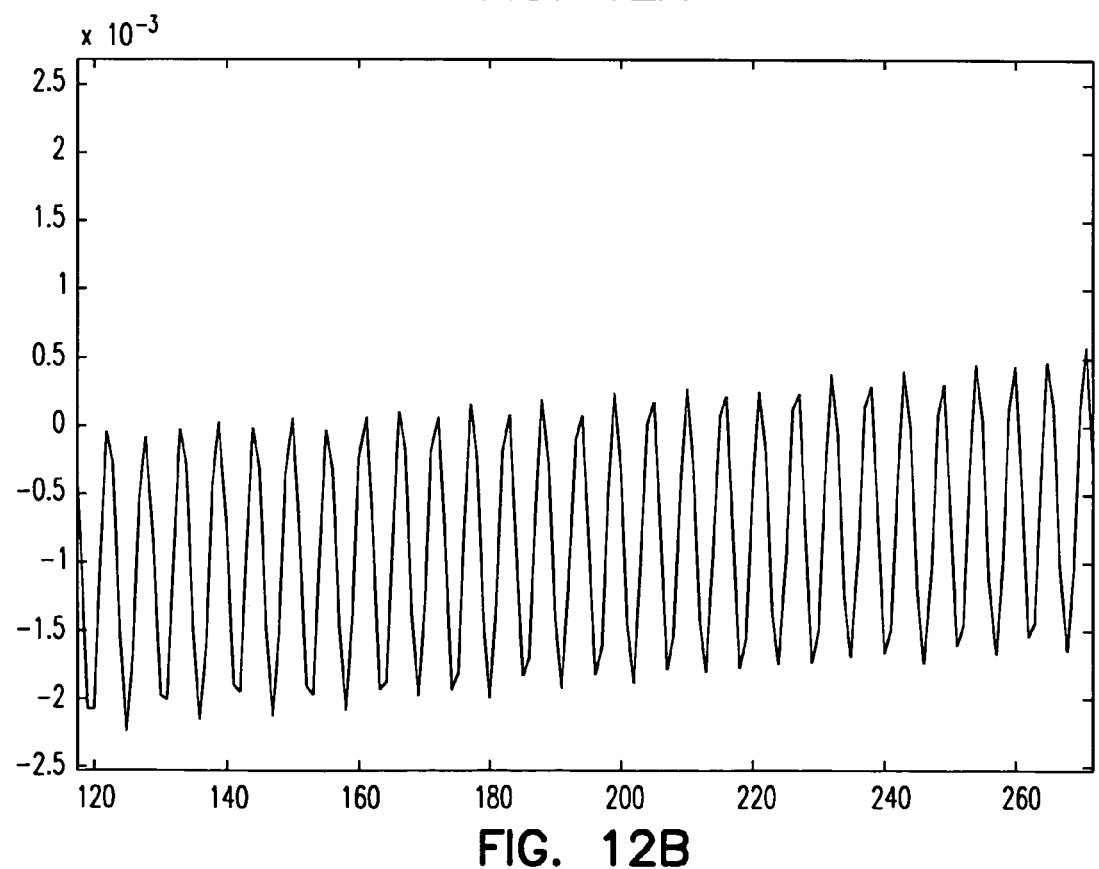
FIG. 12*b* illustrates a graph depicting a zoomed in picture of FIG. 11*b*.
Figure 12C:
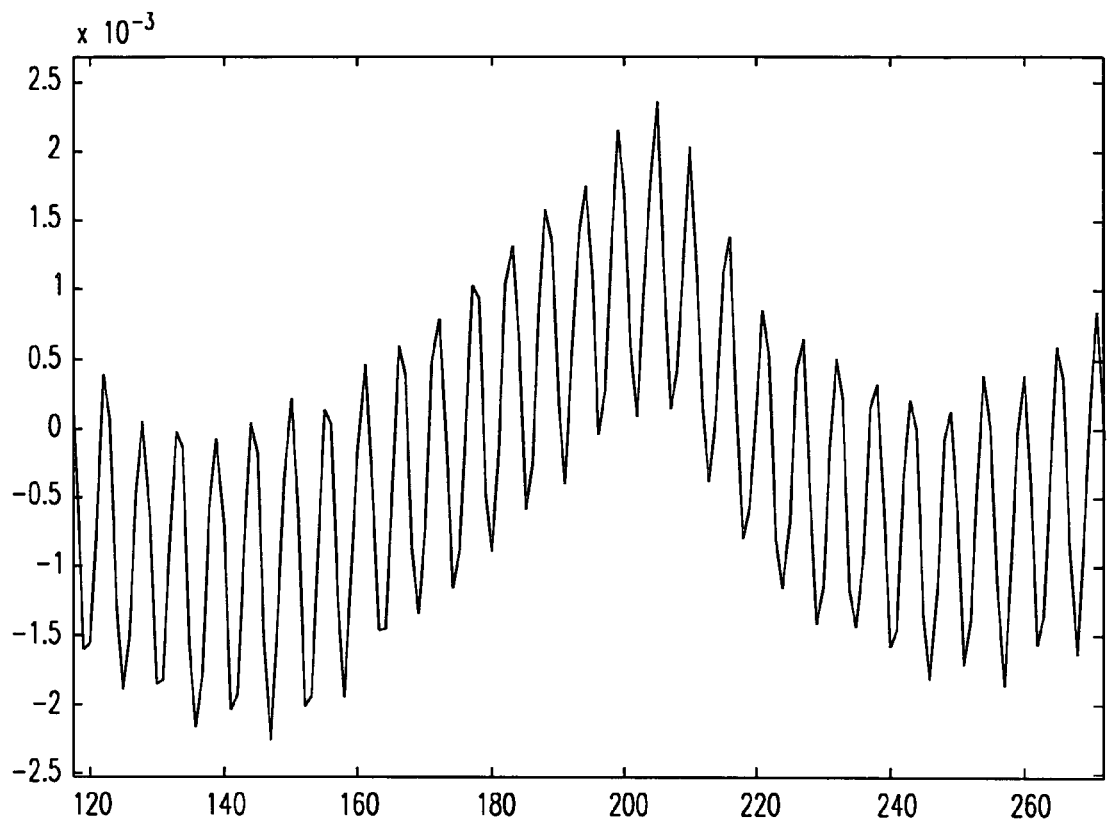
FIG. 12*c* illustrates a graph depicting a zoomed in picture of FIG. 11*c*.
Figure 12D:
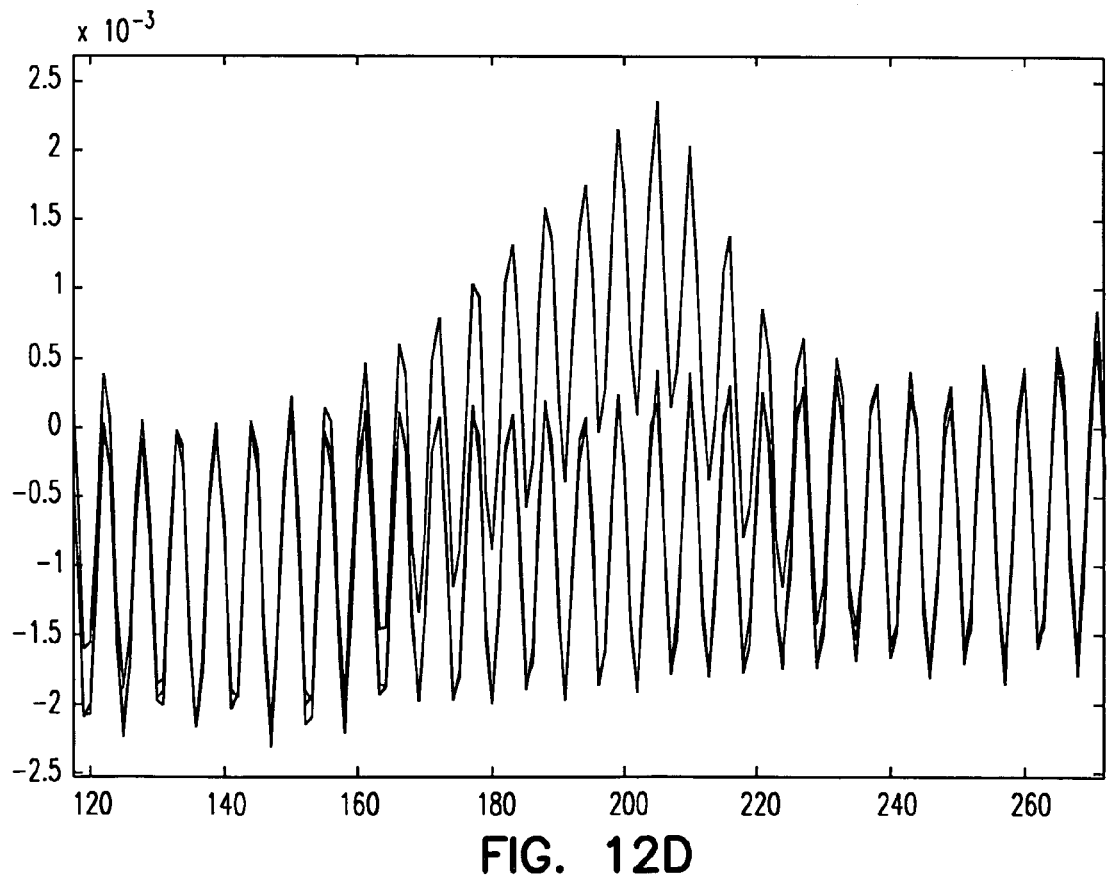
FIG. 12*d* illustrates a graph depicting a zoomed in picture of FIG. 11*d*.

FIG. 11a illustrates a graph depicting the actual background. FIG. 11b illustrates a graph depicting the simulation background. FIG. 11c illustrates a graph depicting the residual. FIG. 11d displays a graph of an actual background spectrum, the principal component analysis fit (intrinsic dimensionality) of the background and the residual spectrum produced from the subtraction of at least part of the simulation spectrum from at least part of the experimental spectrum. The graph displays the clear difference between the background and residual, which contains interferences that may be present in the experimental sample, but not in the background. The graph shows the usefulness of characterizing and eliminating etalon noise in that the simulation spectrum will have a better fit to the experimental spectrum with the removal of a significant source of noise and interference. The embodiments of the present invention may reduce the interference from noise by about two to three magnitudes over traditional methods. FIGS. 12a-d display zoomed in portions of the graphs FIGS. 11a-d.

Figure 13A:
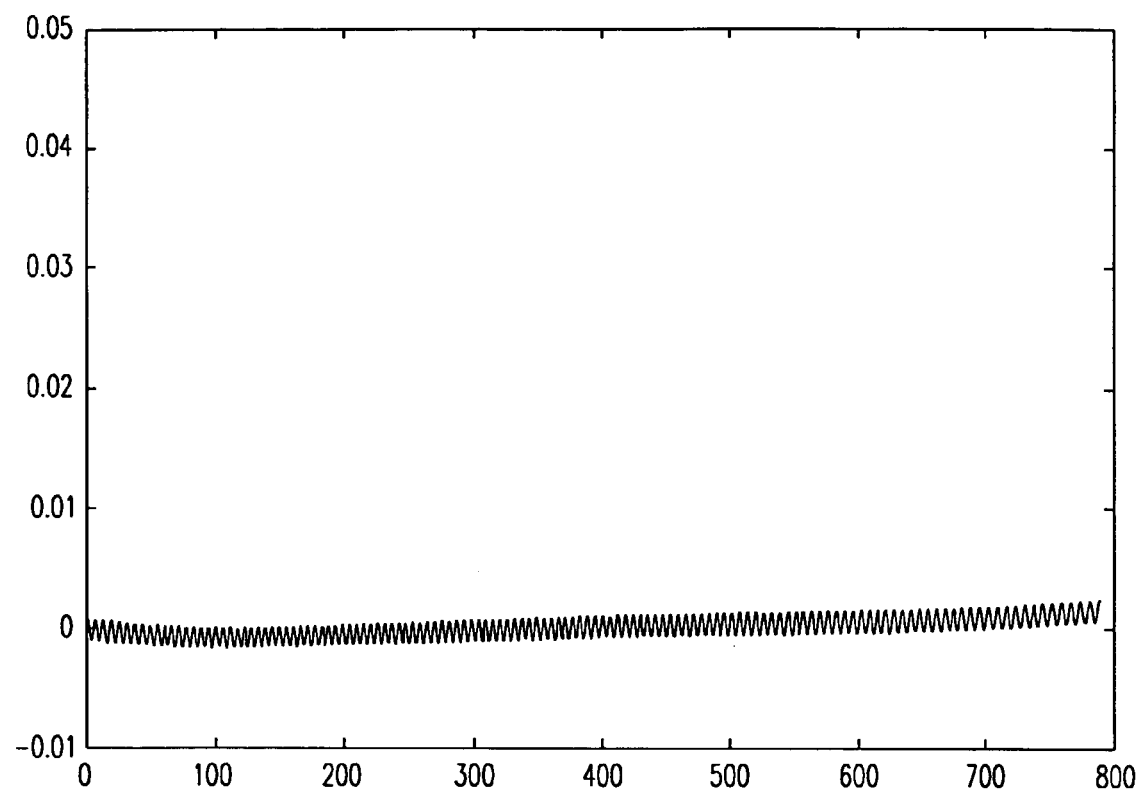
FIG. 13*a* illustrates a graph depicting a simulation etalon background.
Figure 13B:
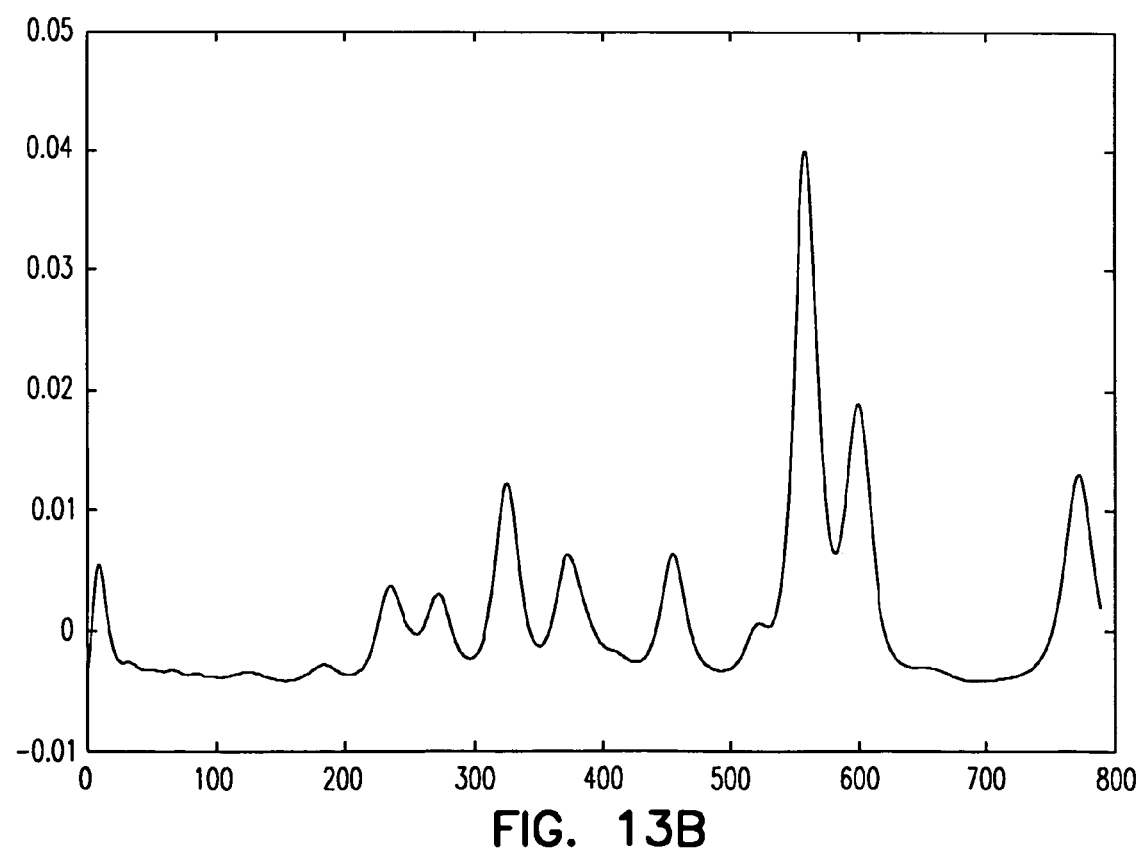
FIG. 13*b* illustrates a graph depicting an experimental spectrum.
Figure 13C:
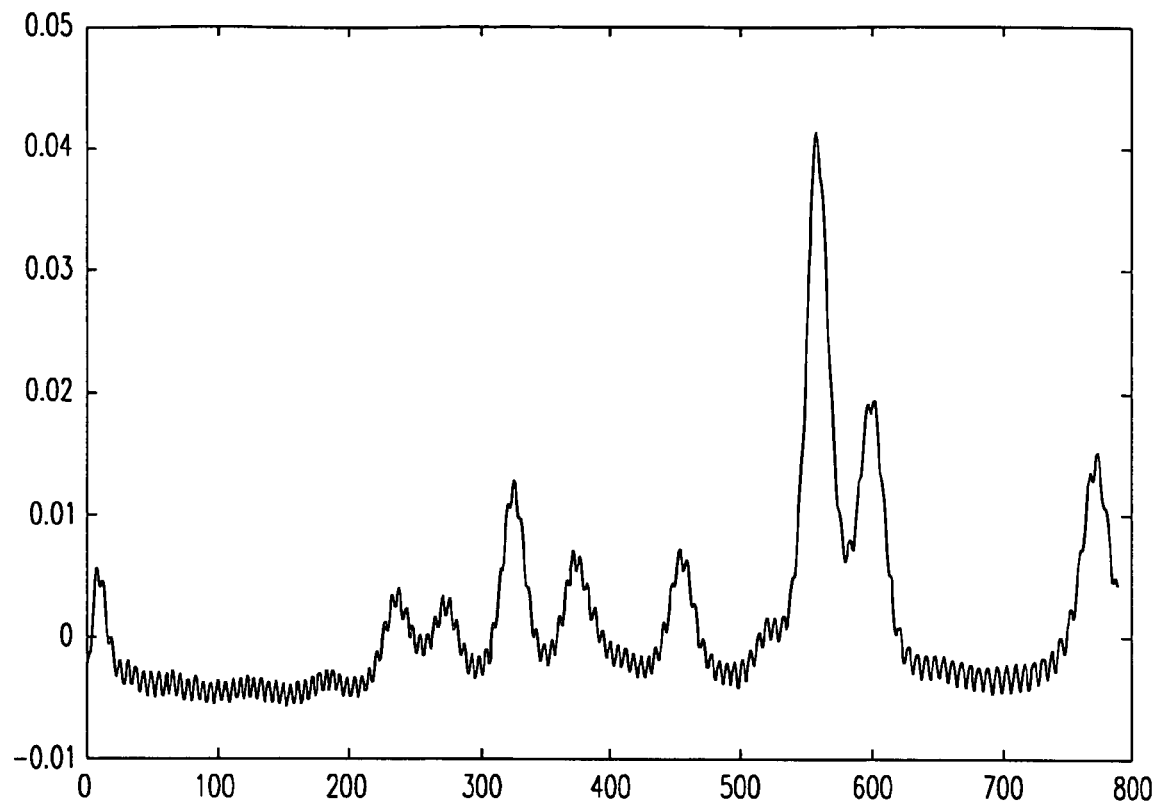
FIG. 13*c* illustrates a graph depicting a simulation spectrum.
Figure 13D:
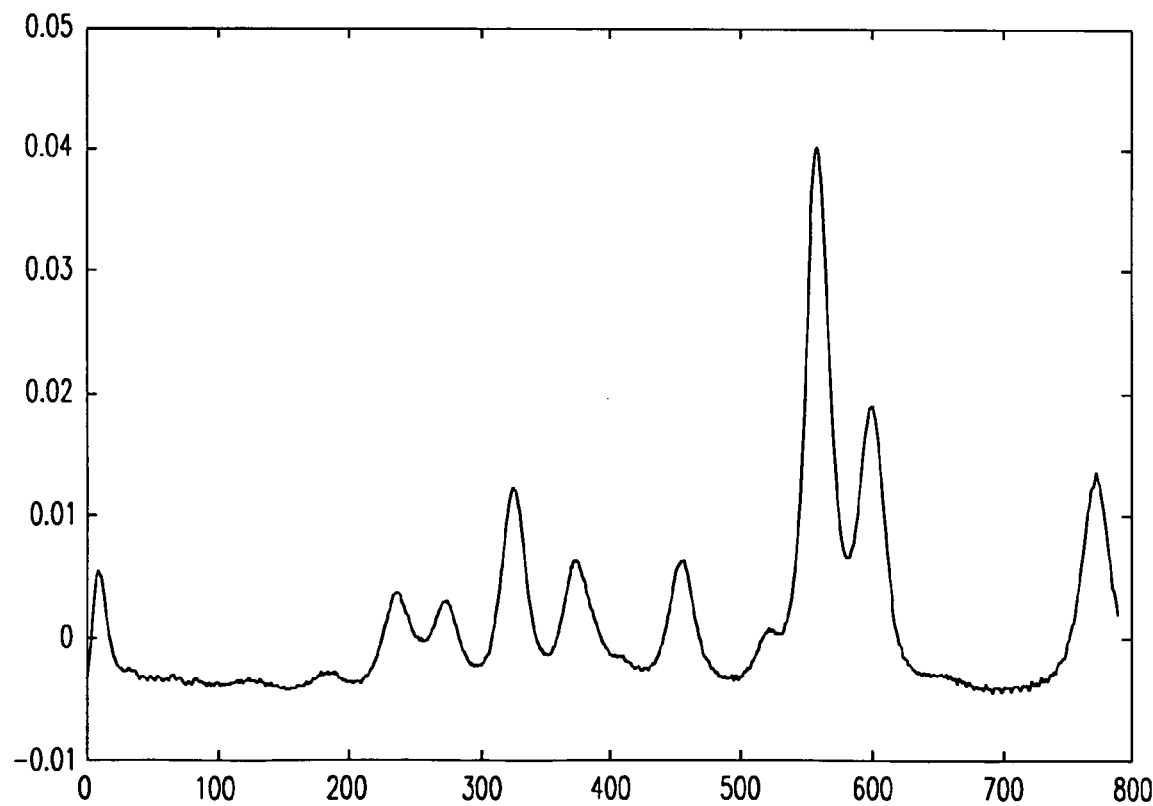
FIG. 13*d* illustrates a graph depicting an etalon corrected experimental spectrum.
Figure 13E:
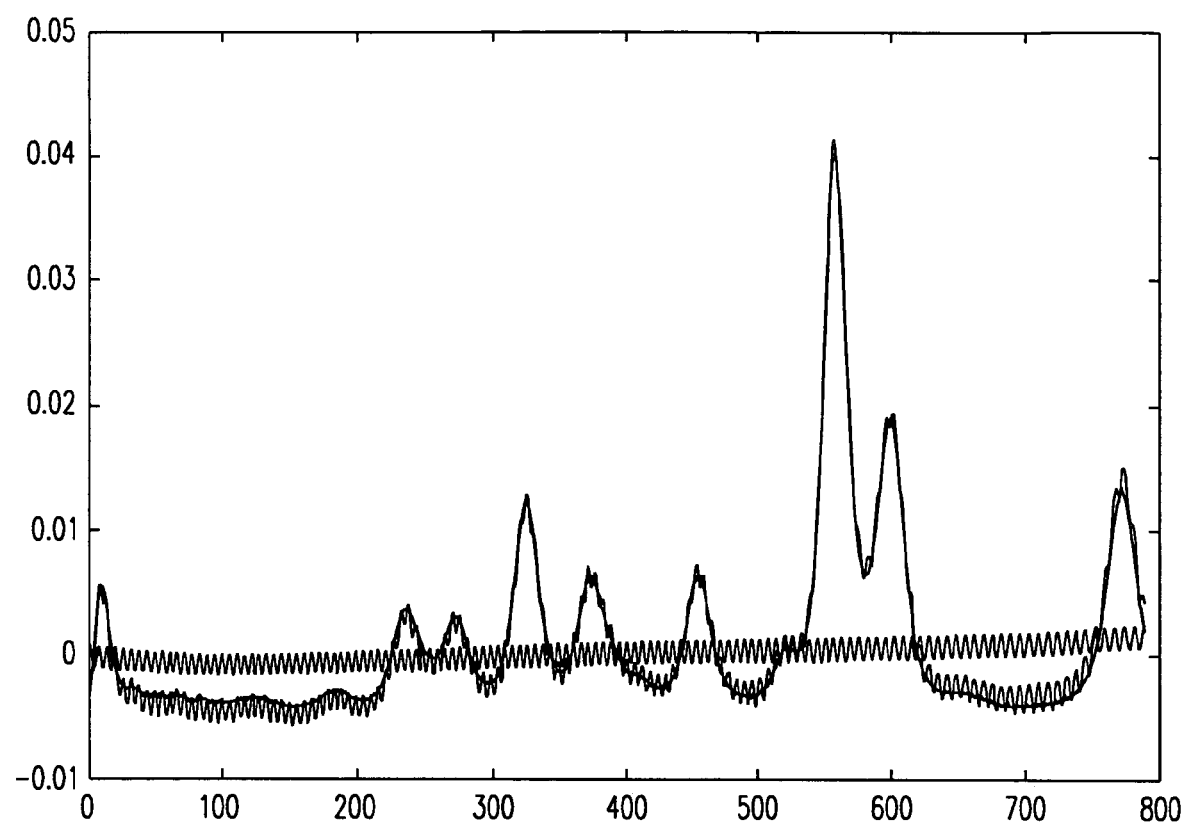
FIG. 13*e* illustrates a graph depicting a simulation etalon background, an experimental spectrum, a simulation spectrum and an etalon corrected experimental spectrum.
Figure 14A:
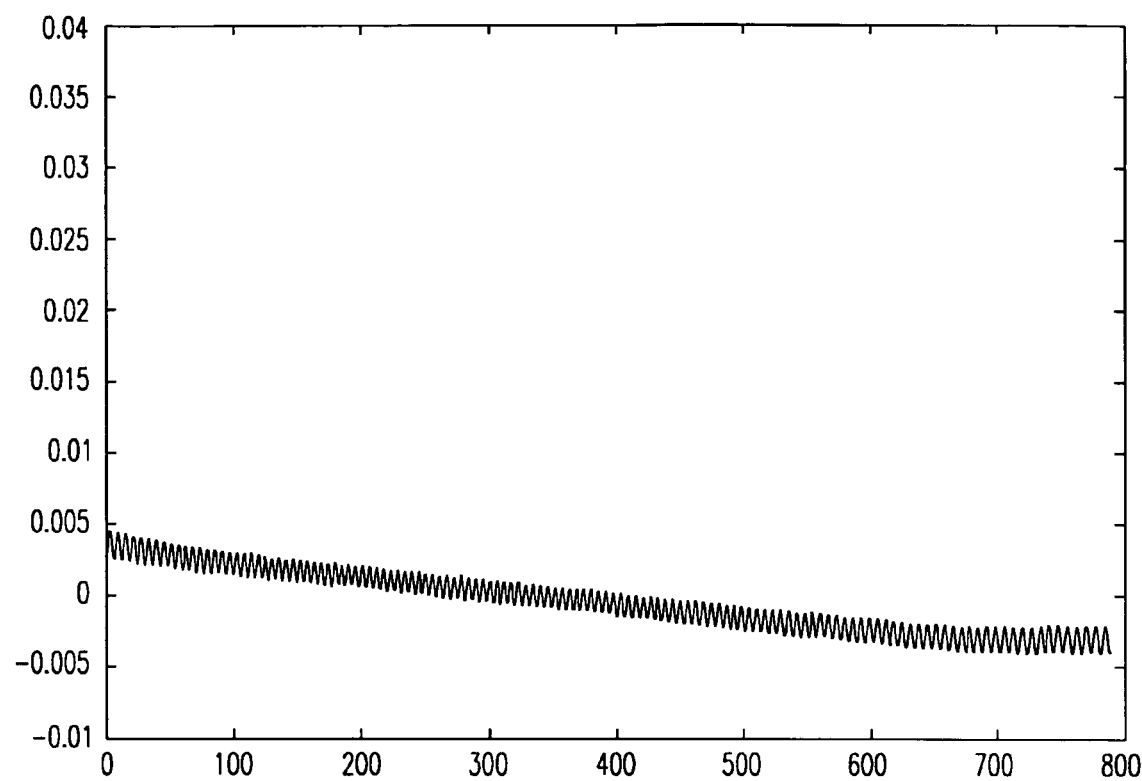
FIG. 14*a* illustrates a graph depicting FIG. 13*a*, but with a changing etalon background.
Figure 14B:
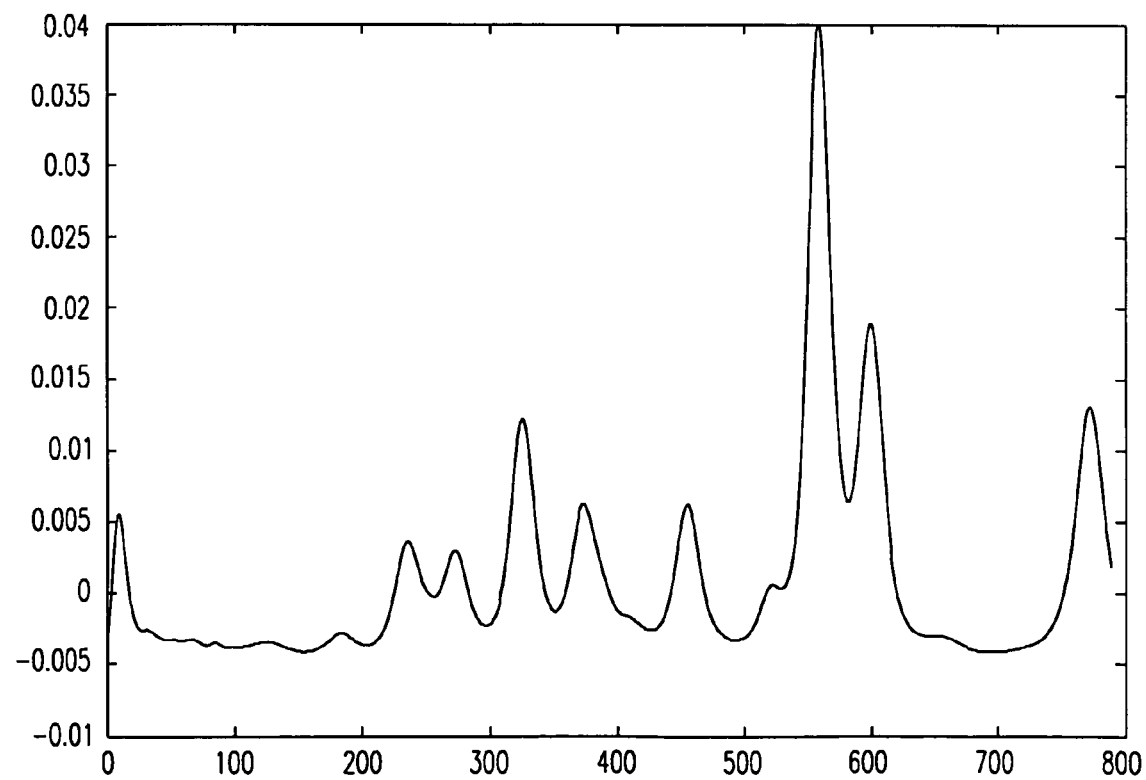
FIG. 14*b* illustrates a graph depicting FIG. 13*b*, but with a changing etalon background.
Figure 14C:
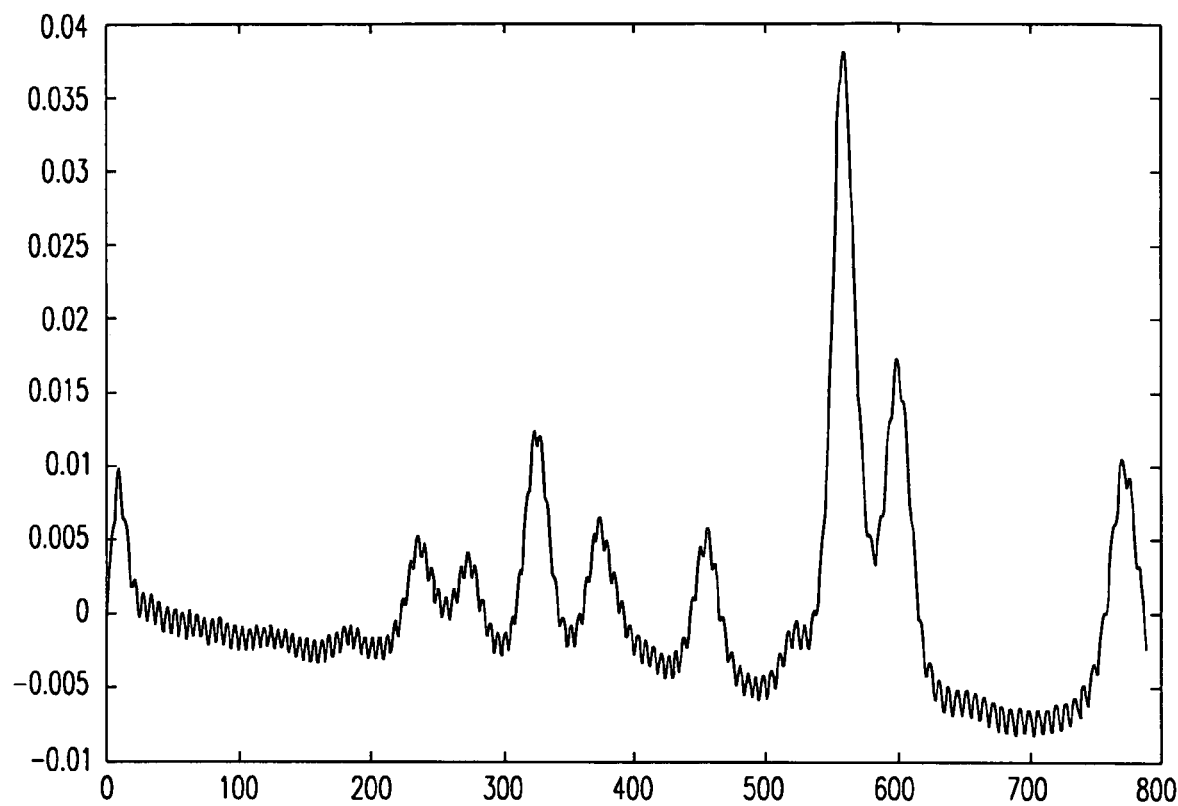
FIG. 14*c* illustrates a graph depicting FIG. 13*c*, but with a changing etalon background.
Figure 14D:
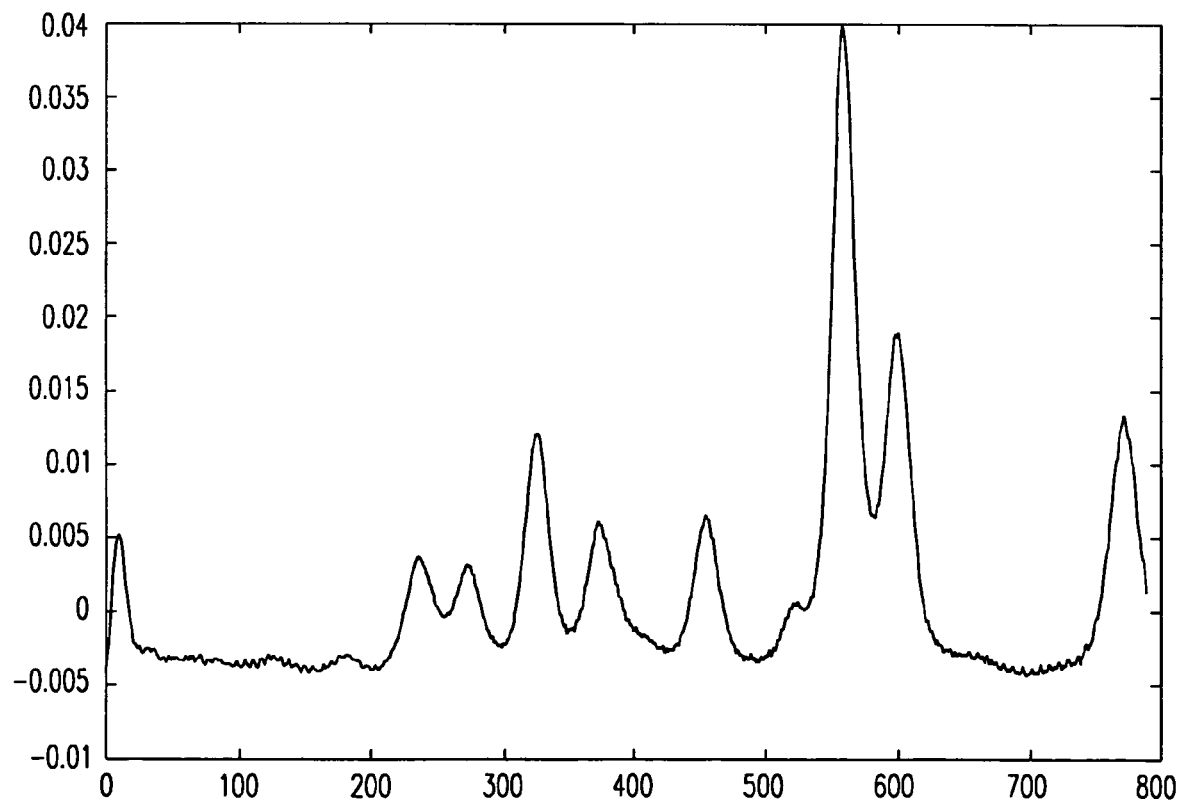
FIG. 14*d* illustrates a graph depicting FIG. 13*d*, but with a changing etalon background.
Figure 14E:
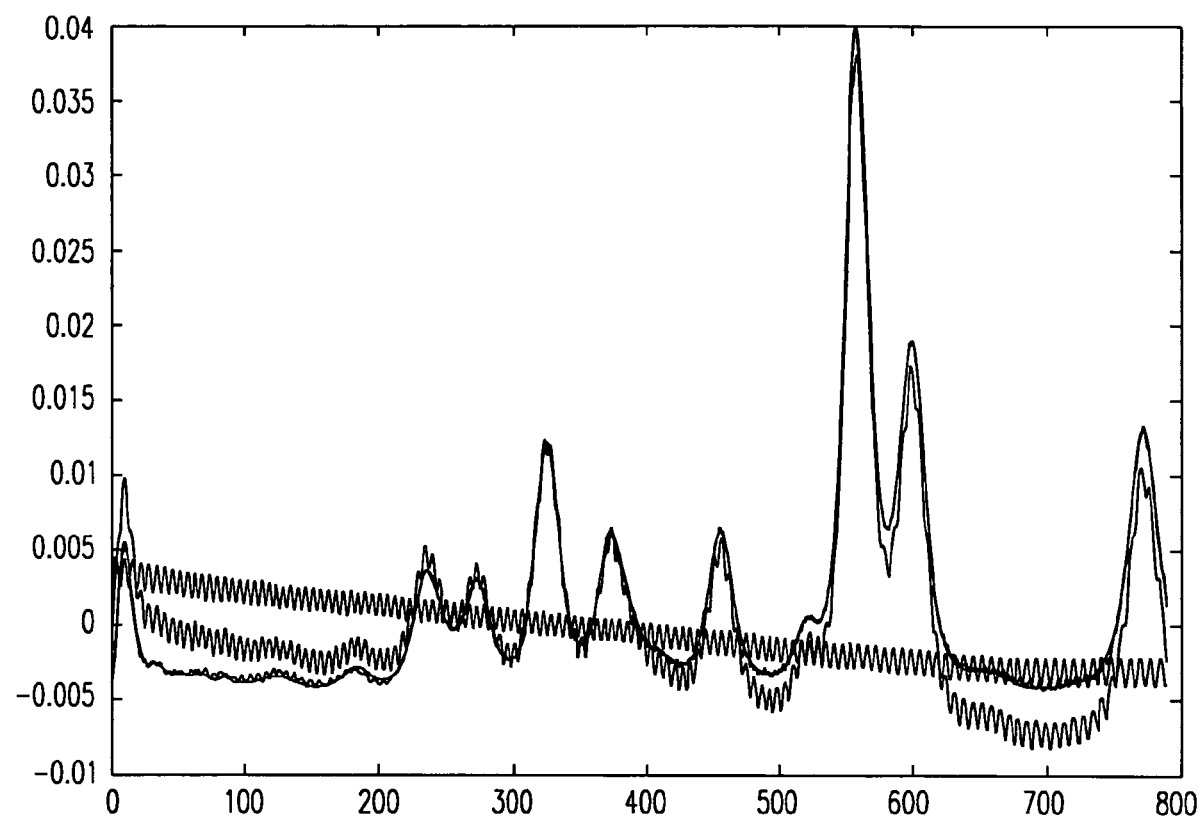
FIG. 14e illustrates a graph depicting FIG. 13e, but with a changing etalon background.

FIG. 13a illustrates a graph depicting a simulation etalon background. FIG. 13b illustrates a graph depicting an experimental spectrum. FIG. 13c illustrates a graph depicting a simulation spectrum. FIG. 13d illustrates a graph depicting an etalon corrected experimental spectrum. FIG. 13e displays an experimental spectrum, simulation spectrum, etalon spectrum and the experimental spectrum with reduced noise. Although the experimental spectrum and simulation spectrum fit reasonably well, by subtracting the etalon spectrum from the experimental spectrum, the closest fit is between the experimental spectrum with reduced noise and the simulation spectrum. The closer the fit between the simulation spectrum and experimental spectrum with reduced noise, the more accurate the analysis becomes. FIGS. 14a-e display the same spectra as FIGS. 13a-e except that the background spectrum has changed over a period of five minutes. The resulting fit between the simulation spectrum and experimental spectrum with reduced noise (FIG. 14e) is much worse than that shown in FIG. 13e. The lack of fit would indicate to the operator that the background has changed and another intrinsic dimension analysis must be performed on the background. This figure displays the advantage of the embodiments of the present invention in that the background fit can be adjusted in real time due to the quickness of this method. Previous attempts to take background readings and make adjustments were on the order of minutes. Further, the embodiments of the invention allow an operator to characterize the background in a single step and reduces or removes the need to scan for a background sample before every sample scan taken.

Figure 15:
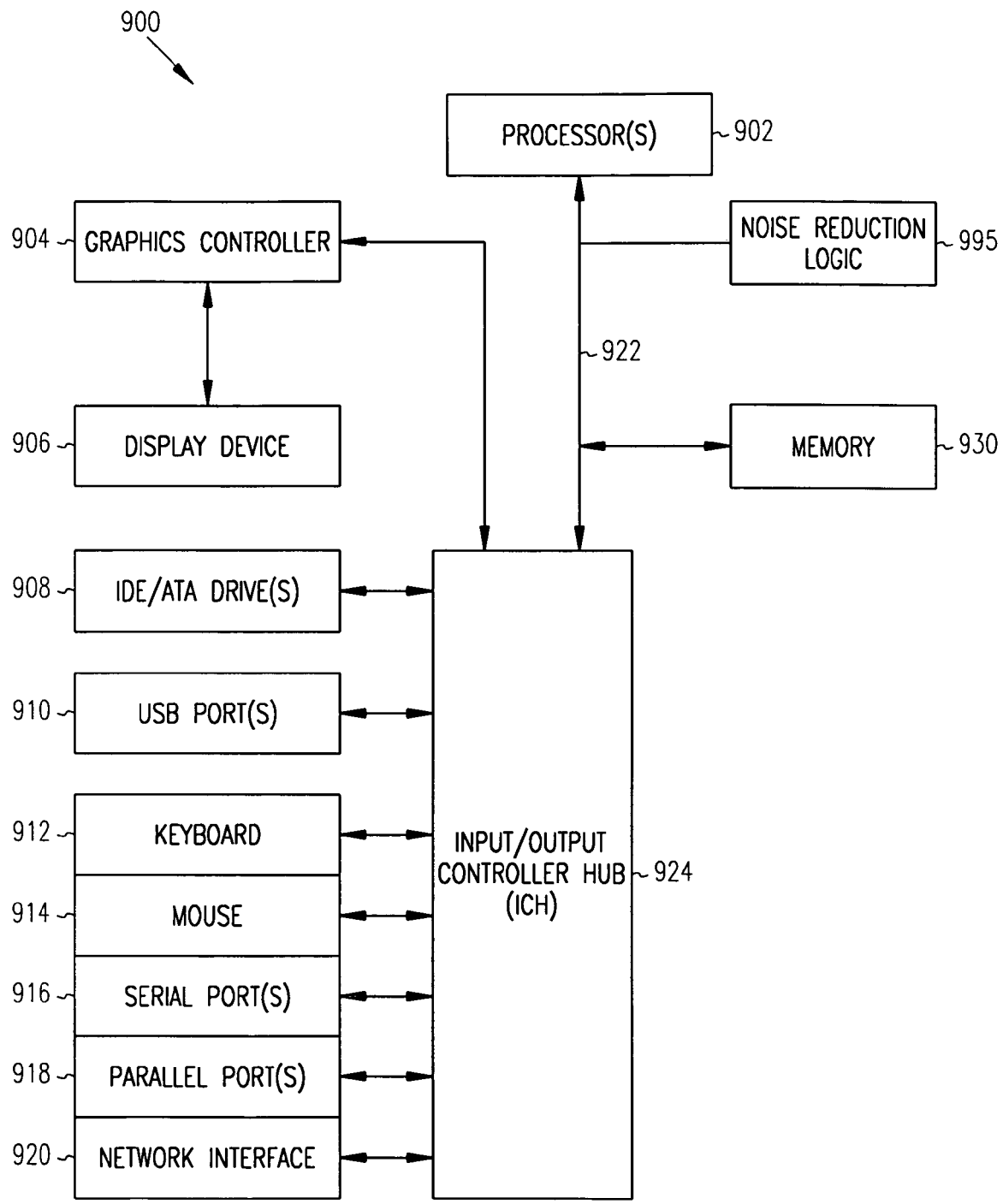
FIG. 15 illustrates a computer system used in conjunction with some embodiments of the invention.

This section provides an overview of hardware and the operating environment in which some embodiments of the invention can be practiced. FIG. 15 illustrates a computer system used in conjunction with some embodiments of the invention. As illustrated in FIG. 15, a computer system 900 comprises processor(s) 902. The computer system 900 also may include a memory unit 930, a processor bus 922, and an Input/Output controller hub (ICH) 924. The processor(s) 902, the memory unit 930, and the ICH 924 are coupled to the processor bus 922. The processor(s) 902 may comprise any suitable processor architecture. The computer system 900 may comprise one, two, three, or more processors, any of which may execute a set of instructions in accordance with at least some embodiments of the invention.

In some embodiments, the computer system 900 includes a machine-readable medium that stores a set of instructions (e.g., software) embodying any one, or all, of the methodologies to reduce background noise in an experimental spectrum. For example, a noise reduction logic 995 may be software.

The memory unit 930 stores data and/or instructions, and may comprise any suitable memory, such as a dynamic random access memory (DRAM), for example. The computer system 900 also may include IDE drive(s) 908 and/or other suitable storage devices. Although not shown, the memory unit 930, the processor(s) 902 and/or the IDE drive(s) 908 may include at least a part of the noise reduction logic 995. A graphics controller 904 controls the display of information on a display device 906, according to some embodiments of the invention.

The input/output controller hub (ICH) 924 provides an interface to I/O devices or peripheral components for the computer system 900. The ICH 924 may comprise any suitable interface controller to provide for any suitable communication link to the processor(s) 902, the memory unit 930 and/or to any suitable device or component in communication with the ICH 924. For one embodiment, the ICH 924 provides suitable arbitration and buffering for each interface.

For some embodiments, the ICH 924 provides an interface to one or more suitable integrated drive electronics (IDE) drives 908, such as a hard disk drive (HDD) or compact disc read only memory (CD ROM) drive, or to suitable universal serial bus (USB) devices through one or more USB ports 910. For some embodiments, the ICH 924 also provides an interface to a keyboard 912, a mouse 914, a CD-ROM drive 918, one or more suitable devices through one or more firewire ports 916. For one embodiment, the ICH 924 also provides a network interface 920 though which the computer system 900 can communicate with other computers and/or devices.

In the description, numerous specific details such as logic implementations, opcodes, means to specify operands, resource partitioning/sharing/duplication implementations, types and interrelationships of system components, and logic partitioning/integration choices are set forth in order to provide a more thorough understanding of the embodiments of the present invention. It will be appreciated, however, by one skilled in the art that embodiments of the invention may be practiced without such specific details. In other instances, control structures, gate level circuits and full software instruction sequences have not been shown in detail in order not to obscure the embodiments of the invention. Those of ordinary skill in the art, with the included descriptions will be able to implement appropriate functionality without undue experimentation.

Embodiments of the invention include features, methods or processes that may be embodied within machine-executable instructions provided by a machine-readable medium. A machine-readable medium includes any mechanism which provides (i.e., stores and/or transmits) information in a form accessible by a machine (e.g., a computer, a network device, a personal digital assistant, manufacturing tool, any device with a set of one or more processors, etc.). In an exemplary embodiment, a machine-readable medium includes volatile and/or non-volatile media (e.g., read only memory (ROM), random access memory (RAM), magnetic disk storage media, optical storage media, flash memory devices, etc.), as well as electrical, optical, acoustical or other form of propagated signals (e.g., carrier waves, infrared signals, digital signals, etc.)).

A number of figures show block diagrams of systems and apparatus to reduce background noise in an experimental spectrum, in accordance with some embodiments of the invention. A number of figures show flow diagrams illustrating operations for reduction of background noise in an experimental spectrum, in accordance with some embodiments of the invention. The operations of the flow diagrams will be described with references to the systems/apparatus shown in the block diagrams. However, it should be understood that the operations of the flow diagrams could be performed by embodiments of systems and apparatus other than those discussed with reference to the block diagrams, and embodiments discussed with reference to the systems/apparatus could perform operations different than those discussed with reference to the flow diagrams.

In view of the wide variety of permutations to the embodiments described herein, this detailed description is intended to be illustrative only, and should not be taken as limiting the scope of the invention. What is claimed as the invention, therefore, is all such modifications as may come within the scope and spirit of the following claims and equivalents thereto. Therefore, the specification and drawings are to be regarded in an illustrative rather than a restrictive sense.

Those skilled in the art will recognize that digital light processing, other optical processing methods, and other means of processing may be substituted for or supplement electrical signal processes. While significant applications focus on spectroscopy involving radiation, this technique may be equally applicable to spectroscopy using other types of energy e.g. acoustic, seismic, mechanical vibrations, with applications to the seismic industry, audio recording and medical imaging etc.

The invention claimed is:

1. A method to reduce background noise comprising at least one of random noise and structured noise in a sample substance spectrum, the method comprising:
   (a) contacting a blank sample with electromagnetic radiation, sufficient to obtain a background spectrum;
   (b) performing an intrinsic dimension analysis on the background spectrum, sufficient to obtain multiple correlations between variables in the background spectrum;
   (c) identifying and retaining the intrinsic dimensionality of the variables in the background spectrum;
   (d) contacting a sample of the substance with electromagnetic radiation, sufficient to obtain a sample spectrum exhibiting said background noise;
   (e) performing a regression analysis on the sample spectrum, based upon known characteristics of pure substances, effective to provide a simulation spectrum;
   (f) mathematically operating at least part of the simulation spectrum with at least part of the sample spectrum effective to provide a residual spectrum;
   (g) projecting at least part of the residual spectrum onto the intrinsic dimensionality of the background spectrum, effective to identify any etalons present in the residual spectrum;
   (h) mathematically operating the etalon with the sample spectrum, effective to provide a substance sample spectrum having reduced background noise; and
   (i) storing the spectrum of the substance sample having reduced background noise into a machine-readable medium.

2. The method of claim 1, wherein the background noise in the substance sample spectrum is reduced by at least about 2 orders of magnitude.

3. The method of claim 1, wherein the background noise in the substance sample spectrum is reduced by at least about 3 orders of magnitude.

4. The method of claim 1, wherein the background noise comprises random noise and structured noise.

5. The method of claim 1, wherein the background noise comprises solely structured noise.

6. The method of claim 1, wherein the substance spectrum is an absorbance spectrum or spectrum in which interference patterns cause a varying background.

7. The method of claim 1, wherein the substance sample spectrum is obtained from or collected by a spectroscopic device.

8. The method of claim 7, wherein the spectroscopic device is a laser spectroscopic device.

9. The method of claim 1, wherein the electromagnetic radiation is infrared energy.

10. The method of claim 9, wherein the infrared energy is near-infrared energy.

11. The method of claim 9, wherein the infrared energy is mid-infrared energy.

12. The method of claim 1, wherein the contacting of the blank sample with the electromagnetic radiation is in-line.

13. The method of claim 1, wherein the contacting of the blank sample with the electromagnetic radiation is static.

14. The method of claim 1, wherein the intrinsic dimension analysis is principal component analysis (PCA).

15. The method of claim 1, wherein the intrinsic dimension analysis is singular value decomposition (SVD).

16. The method of claim 1, wherein the intrinsic dimension analysis is eigenfactor analysis.

17. The method of claim 1, wherein the intrinsic dimension analysis is neural networks.

18. The method of claim 1, wherein the intrinsic dimension analysis is a pattern recognition technique.

19. The method of claim 1, wherein the intrinsic dimension analysis is a technique that determines intrinsic dimensionality.

20. The method of claim 1, wherein the intrinsic dimension analysis is a wavelet analysis.

21. The method of claim 1, wherein the multiple correlations are numbers and vectors describing the significance of the relationship between two variables.

22. The method of claim 1, wherein the variables in the background spectrum are one or more of a group including absorbance intensity, concentrations of sample and interferents, wavelength range, component structure, inter-molecular attractions and distortions.

23. The method of claim 1, wherein certain of the correlations are stronger than others, the stronger correlations include the strongest produced by the intrinsic dimension analysis method describing the relationship between two variables.

24. The method of claim 1, wherein the regression analysis is multivariate curve resolution—alternating least squares (MCR-ALS).

25. The method of claim 1, wherein the regression analysis is principal component regression.

26. The method of claim 1, wherein the regression analysis is partial least squares.

27. The method of claim 1, wherein the regression analysis is projection of latent structures.

28. The method of claim 1, wherein the regression analysis is linear least squares.

29. The method of claim 1, wherein the regression analysis is the solution of simultaneous equations.

30. The method of claim 1, wherein the regression analysis is non-linear least squares.

31. The method of claim 1, wherein the regression analysis is linear regression.

32. The method of claim 1, wherein the regression analysis is non-linear regression.

33. The method of claim 1, wherein known characteristics of pure substances may be represented by unique features in a spectrum.

34. The method of claim 1, further comprising after step (h), the step of performing a regression analysis on the background corrected spectrum.

35. The method of claim 34, further comprising after performing the regression analysis on the background corrected spectrum, the step of repeatedly performing a regression analysis on the background corrected spectrum until the difference in spectra becomes sufficiently small.

36. The method of claim 1, wherein the signal to noise ratio (S/N) is increased by an order of at least about 2.

37. The method of claim 1, wherein the signal to noise ratio (S/N) is increased by an order of at least about 3.

38. The method of claim 1, wherein the machine-readable medium comprises a memory.

39. A method to reduce, by at least about 2 orders of magnitude, background noise comprising at least one of random noise and structured noise in a sample absorbance spectrum of a substance, the method comprising:
(a) contacting a blank sample with infrared energy, sufficient to obtain a background spectrum;
(b) performing a principal component analysis (PCA) on the background spectrum, sufficient to obtain multiple correlations between variables in the background spectrum;
(c) identifying and retaining the intrinsic dimensionality of the variables in the background spectrum;
(d) contacting a sample of the substance with infrared energy, sufficient to obtain a sample spectrum exhibiting said background noise;
(e) performing a multivariate curve resolution-alternating least squares (MCR-ALS) analysis on the sample spectrum, based upon known characteristics of pure substances, effective to provide a simulation spectrum;
(f) subtracting at least part of the simulation spectrum from at least part of the sample spectrum, effective to provide a residual spectrum;
(g) projecting at least part of the residual spectrum onto the intrinsic dimensionality of the background spectrum, effective to identify any etalons present in the residual spectrum;
(h) removing the etalon from the sample spectrum, effective to provide a substance sample spectrum having reduced background noise; and
(i) storing the spectrum of the substance sample having reduced background noise into a machine-readable medium.

40. The method of claim 39, wherein the machine-readable medium comprises a memory.

41. A method to reduce background noise comprising at least one of random noise and structured noise in a sample spectrum of a substance, the method comprising:
(a) contacting a blank sample with electromagnetic radiation, sufficient to obtain a background spectrum;
(b) performing an intrinsic dimension analysis on the background spectrum, sufficient to obtain multiple correlations between variables in the background spectrum;
(c) identifying and retaining the intrinsic dimensionality of the variables in the background spectrum;
(d) contacting a sample of the substance with electromagnetic radiation, sufficient to obtain a sample spectrum exhibiting undesirable background noise;
(e) performing an intrinsic dimension analysis on the background spectrum and sample spectrum simultaneously, sufficient to obtain multiple correlations between variables in the background spectrum and sample spectrum;
(f) identifying and retaining the common intrinsic dimensionality of the variables in the background spectrum and sample spectrum;
(g) projecting the common intrinsic dimensionality of the background and sample spectra onto the intrinsic dimensionality of the background spectrum, sufficient to provide a residual spectrum;
(h) mathematically operating the residual spectrum with the sample spectrum, effective to provide a sample spectrum of the substance having reduced background noise; and
(i) storing the spectrum of the substance sample having reduced background noise into a machine-readable medium.

42. The method of claim 41, wherein the machine-readable medium comprises a memory.

43. A method to reduce background noise comprising at least one of random noise and structured noise in a sample spectrum of a substance, the method comprising:
(a) contacting a blank sample with electromagnetic radiation, sufficient to obtain a background spectrum;
(b) performing an intrinsic dimension analysis on the background spectrum, sufficient to obtain multiple correlations between variables in the background spectrum;
(c) identifying and retaining the intrinsic dimensionality of the variables in the background spectrum;
(d) contacting a sample of the substance with electromagnetic radiation, sufficient to obtain a sample spectrum exhibiting said background noise;
(e) performing an intrinsic dimension analysis on the background spectrum and sample spectrum simultaneously, sufficient to obtain multiple correlations between variables in the background spectrum and sample spectrum;
(f) identifying and retaining the common intrinsic dimensionality of the variables in the background spectrum and sample spectrum;
(g) projecting the common intrinsic dimensionality of the variables in the background and sample spectra onto the background spectrum, sufficient to provide a residual spectrum;
(h) performing an intrinsic dimension analysis on the background and residual spectra simultaneously, sufficient to obtain multiple correlations between variables in the background spectrum and residual spectrum;
(i) identifying and retaining the common intrinsic dimensionality of the variables in the background spectrum and residual spectrum;
(j) re-projecting the common intrinsic dimensionality of the background spectrum and residual spectrum onto the intrinsic dimensionality of the background spectrum, sufficient to provide a second residual spectrum;
(k) mathematically operating the second residual spectrum with the sample spectrum, effective to provide a sample spectrum of the substance having reduced background noise; and
(l) storing the spectrum of the substance sample having reduced background noise into a machine-readable medium.

44. The method of claim 43, wherein the machine-readable medium comprises a memory.

* * * * *